United States Patent
Crosson et al.

(10) Patent No.: US 11,419,515 B2
(45) Date of Patent: *Aug. 23, 2022

(54) APPARATUS AND METHOD FOR TREATMENT OF PAIN WITH BODY IMPEDANCE ANALYZER

(71) Applicant: TrueRelief, LLC, Santa Monica, CA (US)

(72) Inventors: John Crosson, Pacific Palisades, CA (US); David Weinkle, Cypress, CA (US)

(73) Assignee: TrueRelief, LLC, Santa Monica, CA (US)

( * ) Notice: Subject to any disclaimer, the term of this patent is extended or adjusted under 35 U.S.C. 154(b) by 868 days.

This patent is subject to a terminal disclaimer.

(21) Appl. No.: 16/132,032

(22) Filed: Sep. 14, 2018

(65) Prior Publication Data

US 2019/0008410 A1  Jan. 10, 2019

Related U.S. Application Data

(63) Continuation of application No. 13/990,487, filed as application No. PCT/US2011/061451 on Nov. 18, 2011, now Pat. No. 10,085,670.
(Continued)

(51) Int. Cl.
*A61B 5/0531* (2021.01)
*A61B 5/00* (2006.01)
(Continued)

(52) U.S. Cl.
CPC ............ *A61B 5/0531* (2013.01); *A61B 5/053* (2013.01); *A61B 5/4824* (2013.01); *A61B 5/742* (2013.01);
(Continued)

(58) Field of Classification Search
CPC ........ A61B 5/0531; A61B 5/053; A61B 5/742
See application file for complete search history.

(56) References Cited

U.S. PATENT DOCUMENTS 4,977,895 A   12/1990  Tannenbaum
5,045,988 A    9/1991  Gritter
(Continued)

FOREIGN PATENT DOCUMENTS

JP   Hei 10-509600 A    9/1998
JP    2003-062034 A    7/2001
(Continued)

OTHER PUBLICATIONS

Notice of Allowance in corresponding Japanese Patent Application No. 2013-542044, Japanese Patent Office, dated May 17, 2016 (2 pages).
(Continued)

*Primary Examiner* — Allen Porter
*Assistant Examiner* — Yasmeen S Warsi
(74) *Attorney, Agent, or Firm* — Nixon Peabody LLP; Justin D. Swindells

(57) ABSTRACT

A patient treatment unit and method analyzes and treats pain in tissues by applying an electrical pulse train to the affected tissue. The impedance of the affected tissue is measured, and the measured impedance is correlated to a level of pain in the patient. The pulse train is further applied in response to the measured impedance to reduce the patient's pain. The patient treatment unit includes a probe stimulus generator that outputs the pulse train. The treatment unit also includes a pair of probes for contacting the patient's body and receiving the pulse train. The pulse has improved shaping based on isolation of high voltage from a low voltage control. The unit further includes a body impedance analysis circuit that senses voltage and current via the probes when
(Continued)

the probes are contacting the patient and observe the impedance. A monitor is electrically coupled to the body impedance analysis circuit and provides an indication of the measured impedance indicative of the patient's level of pain in real-time.

19 Claims, 13 Drawing Sheets

Related U.S. Application Data

(60) Provisional application No. 61/418,111, filed on Nov. 30, 2010.

(51) Int. Cl.
*A61N 1/36* (2006.01)
*A61H 39/00* (2006.01)
*A61B 5/053* (2021.01)

(52) U.S. Cl.
CPC ......... *A61B 5/7475* (2013.01); *A61H 39/002* (2013.01); *A61N 1/3603* (2017.08); *A61N 1/36021* (2013.01); *A61H 2201/501* (2013.01); *A61H 2201/5046* (2013.01); *A61H 2201/5048* (2013.01); *A61H 2230/655* (2013.01)

(56) References Cited

U.S. PATENT DOCUMENTS

| | | |
|---|---|---|
| 5,645,526 A | 7/1997 | Flower |
| 6,496,725 B2 | 12/2002 | Kamada |
| 7,574,257 B2 | 8/2009 | Rittman, III |
| 7,603,171 B2 | 10/2009 | Eror |
| 7,801,585 B1 | 9/2010 | Weinstock |
| 9,238,138 B2 | 1/2016 | Lee |
| 2005/0033381 A1 | 2/2005 | Carter |
| 2005/0177201 A1* | 8/2005 | Freeman ............... A61N 1/0529 607/46 |
| 2005/0177202 A1 | 8/2005 | Classen |
| 2005/0197555 A1 | 9/2005 | Mouradian |
| 2007/0106342 A1 | 5/2007 | Schumann |
| 2009/0270952 A1 | 10/2009 | Weinstock |

FOREIGN PATENT DOCUMENTS

| | | |
|---|---|---|
| JP | 2001-187035 A | 3/2003 |
| JP | 2004-243047 A | 9/2004 |
| JP | 2010-534114 A | 11/2010 |
| WO | WO 2007/075410 A2 | 7/2007 |
| WO | WO 2010/031055 A1 | 3/2010 |

OTHER PUBLICATIONS

International Search Report corresponding to International Patent Application No. PCT/US2011/061451, Korean Intellectual Property Office, dated Jul. 25, 2012 (6 pages).

International Written Opinion corresponding to International Patent Application No. PCT/US2011/061451, Korean Intellectual Property Office, dated Jul. 25, 2012 (4 pages).

* cited by examiner

APPARATUS AND METHOD FOR TREATMENT OF PAIN WITH BODY IMPEDANCE ANALYZER

TECHNICAL FIELD

The present invention relates to a patient treatment unit and method for analyzing and treating pain in human or animal tissues. More particularly, the invention relates to an apparatus and method for evaluating and treating chronic or acute pain with a dual probe patient treatment unit and display and storage of feedback data during the treatment.

BACKGROUND

Electrical stimulation may be used for pain management. One such therapy is transcutaneous electrical nerve stimulation (TENS) therapy, which provides short-term pain relief. Electrical nerve stimulation and electrothermal therapy may also be used to relieve pain associated with various conditions, including back pain. Additionally, intradiscal electrothermal therapy (IDET) is a treatment option for patients with low back pain resulting from intervertebral disc problems.

Pain is typically attributable to a stimulus on nerve endings, which transmits signal impulses to the brain. This type of pain is referred to as nociceptive pain, a somatic sensation of pain, where a patient is made aware of potential tissue damage by neural processes encoding and processing noxious stimuli. The sensation is initiated by nociceptors that detect mechanical, thermal, or chemical changes above a pain threshold. Once stimulated, a nociceptor transmits a signal within the central nervous system through neurons. Each neuron transmits impulse information about the stimulus on the nerve endings along portions of the central nervous system transmission pathway.

Non-nociceptive pain is referred to as neuropathic pain or neuralgia. Neuralgia is pain produced by a change in neurological structure or function. Unlike nociceptive pain, neuralgia exists with no continuous nociceptive input. That is, neuralgia may develop without any actual impending tissue damage. Neuralgia may involve a disease of the nervous system, including an underlying disease process or injury, or from inflammation, infection, and compression or physical irritation of a nerve. Neuralgia is a form of chronic pain and can be extremely difficult to diagnose and treat.

Pain sensations may be gated naturally, such as when pain sensation is inhibited by activation of large diameter afferent neurons activated by vibration, such as when someone burns their hand, and it is involuntarily shaken in response. Transcutaneous electrical nerve stimulation also employs this technique by applying electrical nerve stimulating impulses from an external stimulator to reduce transmission of pain signals to the brain.

Transcutaneous electrical nerve stimulation (TENS) therapy may be used to treat both nociceptor pain and neuralgia. In TENS therapy, an electrical current is applied through the skin near the source of pain. The current is often delivered via electrodes. The current from the electrodes stimulates nerves in the affected area and sends signals to the brain that activate receptors in the central nervous system to reduce normal pain perception.

In a "*Textbook of Pain*" (Butler & Tanner Ltd., $3^{rd}$ Ed. 1994, pp. 59-62), authors Melzack and Walls proposed a gate theory to describe the manner in which transcutaneous electrical nerve stimulation devices interfere with pain. Melzack and Walls suggest that TENS devices generate an artificial abnormal noise on the neural pathways that are shared with the pain fibers conducting the real pain impulses. When the transmission of pain impulses from that region of the body are received by the central nervous system, the impulses are "gated." That is, the transmission of the pain impulses is altered, changed, or modulated in the central nervous system by the artificial signals. As the central nervous system receives the barrage of signals from the stimulated region of the body, a neurological circuit closes a gate and stops relaying the pain impulses to the brain.

Gating is affected by the degree of activity in the large diameter and the small diameter nerve fibers. Nerve transmissions carried by large nerve fibers travel more quickly than nerve transmissions carried by small nerve fibers. As such, transcutaneous electrical nerve stimulation to large nerve fibers travel to the brain more quickly and are more powerful than pain impulses carried by smaller nerve fibers. Thus, the transcutaneous electrical impulses often arrive at the brain sooner than the pain nerve impulses, and the sensation of the large nerves overrides and blocks out the sensations from the smaller pain nerves. That is, impulses along the larger fibers tend to block pain transmission (close the gates) and more activity in the smaller fibers tends to facilitate transmission (open the gates). The gating mechanism in the spinal cord is affected by descending impulses from the brain. Large fibers may activate specific cognitive processes in the brain, which then influence the gate by downward (descending) impulse transmission.

Another theory regarding the pain reducing effect of transcutaneous electrical nerve stimulation devices is based on the understanding of serotonin and other chemical neurotransmitters that participate in the pain and the pain reduction processes in the central nervous system. Transcutaneous electrical nerve stimulation devices produce their effects by activating opioid receptors in the central nervous system. For example, high frequency transcutaneous electrical nerve stimulation activates delta-opioid receptors both in the spinal cord and supraspinally in the medulla, while low frequency transcutaneous electrical nerve stimulation activates mu-opioid receptors both in the spinal cord and supraspinally. Further high frequency transcutaneous electrical nerve stimulation reduces excitation of central neurons that transmit nociceptive information, reduces release of excitatory neurotransmitters such as glutamate, and increases the release of inhibitory neurotransmitters, including GABA, in the spinal cord, and activates muscarinic receptors centrally to produce analgesia. Low frequency TENS also releases serotonin and activates serotonin receptors in the spinal cord, releases GABA, and activates muscarinic receptors to reduce excitability of nociceptive neurons in the spinal cord.

By applying an electrical field to nervous system tissue, electrical stimulation can effectively reduce or mask certain types of pain transmitted from regions of the body. Pain perception may be inhibited by the applied electrical signals interfering with nerve transmission pathways carrying a pain transmission.

However, electrical stimulation intended to manage or control a pain condition may inadvertently interfere with other nerve transmission pathways in adjacent nervous tissue. Because neurostimulation devices must apply electrical energy across a wide variety of tissues and fluids, the amount of stimulation energy needed to provide the desired amount of pain relief is difficult to precisely control. As such, increasing amounts of energy may be required to ensure sufficient stimulation energy reaches the desired stimulation area. However, as the applied stimulation energy increases, so does the likelihood of damage of surrounding tissue, structures, or neural pathways.

In order to provide pain relief, the targeted tissue must be stimulated, but the applied electrical energy should be properly controlled, and the amount and duration of energy applied to surrounding or otherwise non-targeted tissue must be minimized or eliminated. An improperly controlled electric pulse may not only be ineffective in controlling or managing pain, but it may inadvertently interfere with the proper neural pathways of adjacent spinal nervous tissue.

SUMMARY

One disclosed example is a patient treatment unit for analyzing and treating pain in human or animal tissues. The treatment unit has a probe stimulus generator circuit that outputs a sequence of electrical pulses. The electrical pulses have a pulse width and a pulse frequency and the probe stimulus generator controls the pulse frequency and the pulse width of the electrical pulses. A primary vibrating spherical probe and a secondary spherical probe for contacting a body of a patient are electrically coupled to the probe stimulus generator to receive the sequence of electrical pulses. A body impedance analysis circuit senses voltage or current via the primary vibrating spherical probe and the secondary spherical probe in real-time as the sequence of electrical pulses are applied to the tissues when the probes are contacting the body of the patient. A monitor device is electrically coupled to the body impedance analysis circuit that provides an indication of the sensed voltage or current as an impedance measurement in real-time as the sequence of electrical pulses are applied to the tissues. A display device plots the impedance measurement graphically in real-time.

Another example is a method of displaying real-time impedance data. A sequence of electrical pulses having a pulse width and a pulse frequency is output via a probe stimulus generator circuit. The electrical pulses are received in a primary vibrating spherical probe and a secondary spherical probe. A body of a patient is contacted with the primary and secondary probes. Voltage or current is sensed via the primary vibrating spherical probe and the secondary spherical probe in real-time as the sequence of electrical pulses are applied to the tissues when the probes are contacting the body of the patient via a body impedance analysis circuit. An indication of the sensed voltage or current is provided as an impedance measurement in real-time as the sequence of electrical pulses is applied to the tissues. The measured impedance is displayed graphically in real-time.

Another example is a patient treatment unit for analyzing and treating pain in human or animal tissues. The treatment unit includes a probe stimulus generator circuit including a high voltage generator and a low voltage control circuit that controls the shape of pulses generated by the high voltage generator. The low voltage control circuit is isolated from the high voltage generator. The probe stimulus generator circuit outputs a sequence of electrical pulses having a pulse width and a pulse frequency. The probe stimulus generator controls the pulse frequency and the pulse width of the electrical pulses. A primary vibrating spherical probe and a secondary spherical probe contact a body of a patient and are electrically coupled to the probe stimulus generator to receive the sequence of electrical pulses.

These and other advantages, aspects, and features of the present invention will become more apparent from the following detailed description of embodiments and implementations of the present invention when viewed in conjunction with the accompanying drawings. The present invention is also capable of other embodiments and different embodiments, and details can be modified in various respects without departing from the spirit and scope of the present invention. Accordingly, the drawings and descriptions below are to be regarded as illustrative in nature, and not as restrictive.

BRIEF DESCRIPTION OF THE DRAWINGS

The accompanying drawings illustrate an embodiment of the invention and depict the above-mentioned and other features of this invention and the manner of attaining them. In the drawings:

FIGS. 5A-5D show impedance, power and frequency relationships for a patient treatment unit.

DETAILED DESCRIPTION

Figure 1:
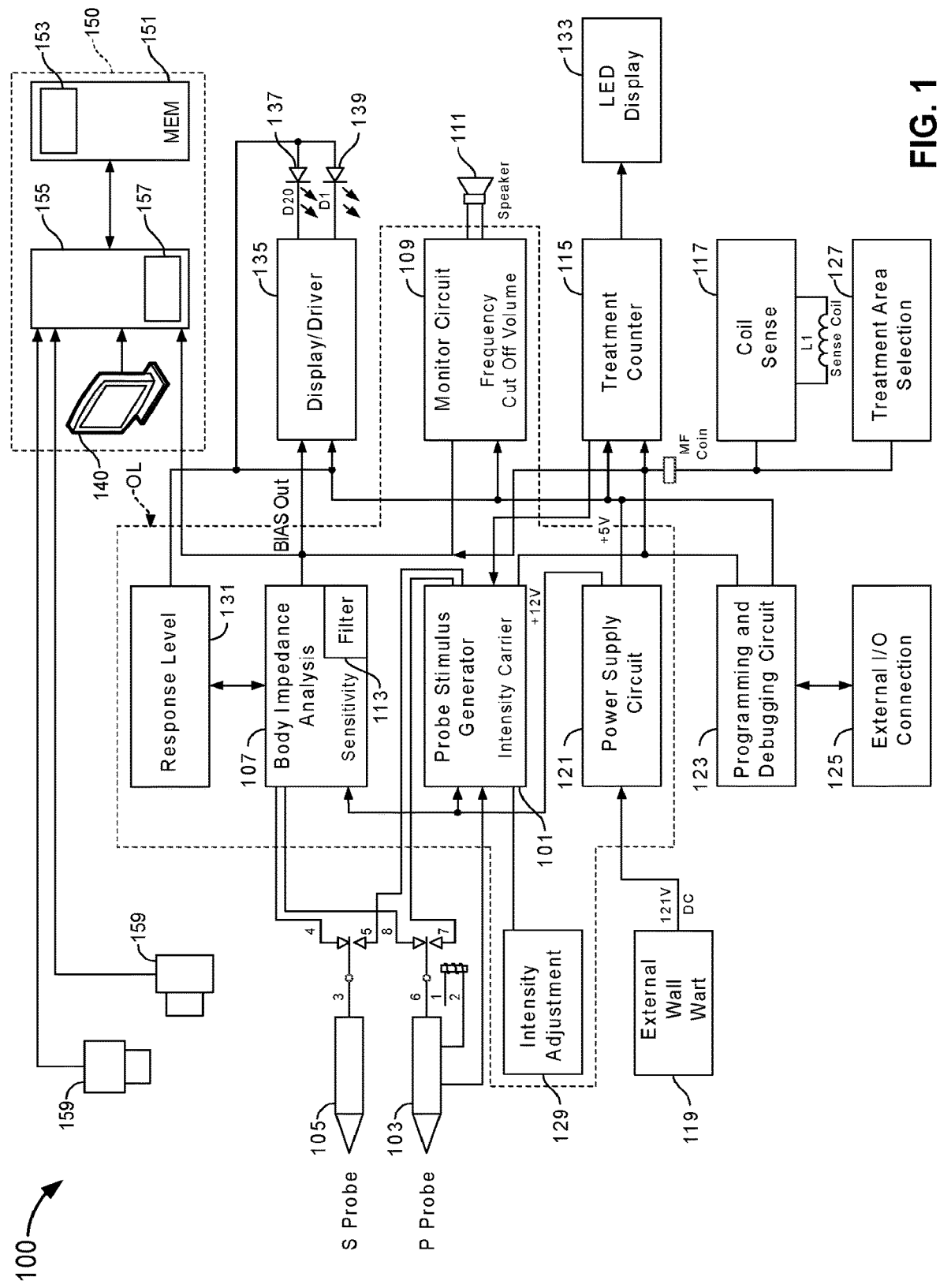
FIG. 1 is a functional block diagram illustrating the circuit components of an example patient treatment unit.

The following detailed description of the invention refers to the accompanying drawings and to certain preferred embodiments, but the detailed description does not limit the invention. The scope of the invention is defined by the appended claims and equivalents as it will be apparent to those of skill in the art that various features, variations, and modifications can be included or excluded based upon the requirements of a particular use.

The patient treatment unit sends an electrical pulse train to the patient's tissues via the primary and secondary probes to provide nerve stimulation to relieve the patient's pain. The patient treatment unit receives impedance measurements from a patient's tissues using primary and secondary probes. As the electrical pulse train is applied, the impedance measurements are monitored. A drop in impedance is indicative of less resistance. The lower impedance measurements have been correlated to lower perceived levels of pain that patients experience. The example patient treatment unit receives impedance information from the patient's tissues, including the body's cellular network. By monitoring the received impedance information as additional electrical pulse trains are applied as pain treatment, the system and method assesses and treats pain experienced by the patient's tissues and other physical structures.

In assessing and treating pain, the system and method applies electrical pulse trains at the site of pain, at the tissue abnormality, or upon selected nervous system trigger points or motor points. These trigger or motor points may also coincide with acupuncture or pressure points of the body. An electrical pulse train is transmitted into the tissue and encounters the inherent impedance signature produced by the tissue or subject matter under study. The impedance information is generated by this initial analysis and measurement and may be used as a baseline measurement to plan and evaluate treatment.

In addition to evaluating and characterizing a patient's degree of pain, the system and method provides therapeutic action to alleviate the pain. The patient treatment unit may provide neural stimulation to alleviate pain, reduce healing time, and upon suitable repetition of therapy, result in long-term improved pain management of the afflicted area.

Pain is reduced or eliminated by means of the electrical pulse train effect on nociceptive afferent neurons, which are sensitive to electrical stimuli as well as noxious stimuli including thermal, mechanical, and chemical stimuli as described above.

An electrical device and method for analyzing and treating abnormality of human and animal tissues includes means for delivering an electrical pulse train having an output voltage in the approximate range of 50-60 volts and a peak pulse amplitude of 190 volts. The means for delivering the electrical pulse train provide a pulse rate range of 1-490 pulses per second or a higher range of 4 kHz to 20 kHz and a pulse duration range of 0.24 to 0.74 milliseconds. Additionally, the means for delivering the electrical pulse train provide a maximum output current of 8.9 milliamps and a maximum charge per pulse of 7 microcoulombs. The electrical pulse train may include complex wave forms with variable frequency, variable pulse width, and AC-coupled rectangular pulses.

The system also includes means for detecting and measuring impedance of the patients' tissues and subjecting the tissues to an electrical pulse train. The system further includes means for generating and applying an electrical pulse train to the tissues to reduce or nullify pain impulse signals perceived by patients.

As outlined above, a patient treatment unit in accordance with the present invention analyzes and treats pain in human or animal tissues by applying an electrical pulse train to the affected tissue. The impedance of the affected tissue is measured, and the measured impedance is correlated to a level of pain in the patient.

FIG. 1 shows a functional block diagram illustrating a patient treatment unit 100 in accordance with the present invention. The patient treatment unit 100 includes a probe stimulus generator 101 that outputs an electrical pulse train sequence. The probe stimulus generator 101 controls the pulse frequency, the pulse width, and the polarity of the electrical pulse train. The pulse width and the carrier current may be varied to control the intensity of the electrical pulse train. Additionally, the probe stimulus generator 101 outputs an electrical pulse train that is a clean waveform, largely free of electrical noise by using rigid electrical component tolerances in a carrier waveform generation circuit. For example, the carrier waveform frequency may be set using a carrier adjustment circuit in combination with a capacitor. This RC circuit may be adjusted to produce the desired carrier frequency of the electrical pulse train. The RC circuit values provide a stable waveform, largely free of electrical noise. Similarly, once the carrier frequency is set, the waveform is not susceptible to frequency drift.

The probe stimulus generator 101 may use a number of different electrical pulse train configurations, depending upon the treatment at hand. For example, a number of different waveforms of variable amplitude may be selected. A basic square wave with a pulse width of 0.24 milliseconds and a pulse rate of 440 pulses per second, with a pulse amplitude of 100 volts, may be selected to treat lower back pain. In addition, the filtering of the electrical pulse train eliminates error signals that often manifest as waveform ripples.

The patient treatment unit 100 includes a primary probe 103 and a secondary probe 105 that are coupled to the probe stimulus generator 101. The treatment unit 100 includes a body impedance analysis circuit 107, a monitor circuit 109, an audio speaker 111, a treatment counter circuit 115, a coils sense circuit 117, a power supply circuit 121, a programming and debugging circuit 123, an external input/output connection interface 125, a treatment area selection circuit 127, an intensity adjustment circuit 129 and a display driver 135. The unit is powered by an external wall wart power supply 119 to supply DC power to the power supply circuit 121. In this example as shown by outline OL in FIG. 1, a number of the circuits 121, 107, 101, 121, 129, 109 may be physically mounted and manufactured on a single printed circuit board to reduce electrical noise between components and circuits. The printed circuit board may be a multi-layer printed circuit board to further reduce ambient electrical noise and to generate a clean and error-free pulse train. As will be explained below, additional useful data may be provided to the clinician via an interface module 150.

Figure 2:
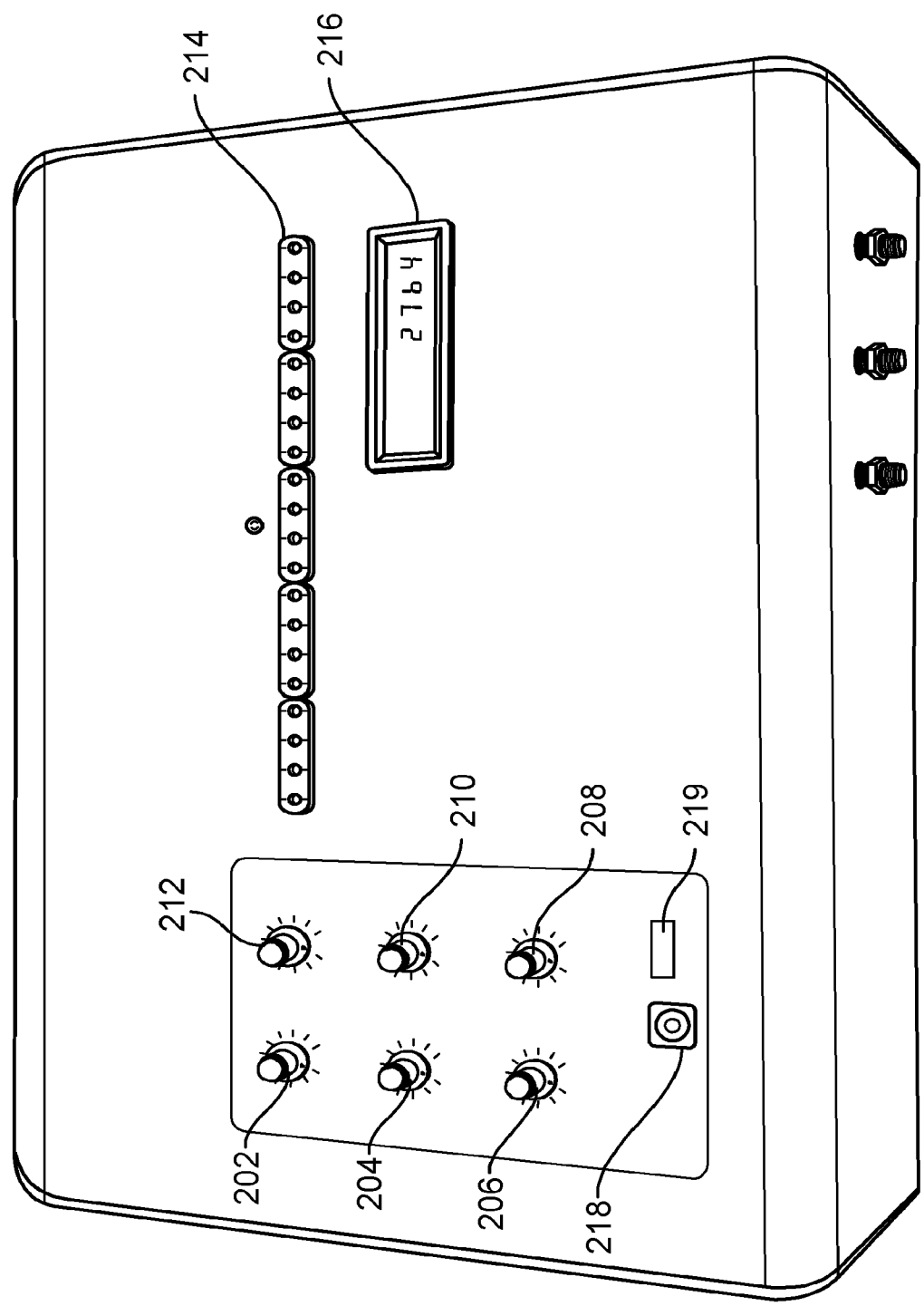
FIG. 2 is a top view illustration of the patient treatment unit in FIG. 1.

FIG. 2 shows an exterior casing 200 of the patient treatment unit 100. The front surface of the exterior casing 200 has a number of controls including a volume knob 202, a tone knob 204, an intensity knob 206, a carrier knob 208, a tone cutoff knob 210, a sensitivity/baseline calibration knob 212, a polarity button 218, and a frequency selector switch 219. The front surface also has an LED contact level impedance display 214 and an algorithmic code display 216 to provide visual indicators of different measurements to the clinician.

The probe stimulus generator 101 also includes internal monitor functions to ensure the safety and performance of patient treatment unit 100. For example, the probe stimulus generator 101 monitors and checks power supply voltage from power supply circuit 121 as well as the coil sense indication from coils sense circuit 117 that the probes 103, 105 are properly connected across a proper tissue or patient. Further, the treatment counter circuit 115 provides a handshake signal indicating a ready condition that must be detected by probe stimulus generator 101 before a pulse train may be applied to a tissue. The probe stimulus generator 101 also includes level shifting circuitry that may be used to alter the carrier current as well as to shift the current and voltage limiting circuitry. The probe stimulus generator 101 will not output the sequence of electrical pulses until the power supply handshake, the coils sense handshake, and the treatment counter handshake signals all indicate that these circuits 121, 117, 115 are in a ready condition.

The pair of probes 103 and 105 receives the electrical pulse train and apply the pulse train to the patient's body. The primary probe 103 and secondary probe 105 are both electrically coupled to the probe stimulus generator 101 to receive the sequence of electrical pulses.

Figure 3A:
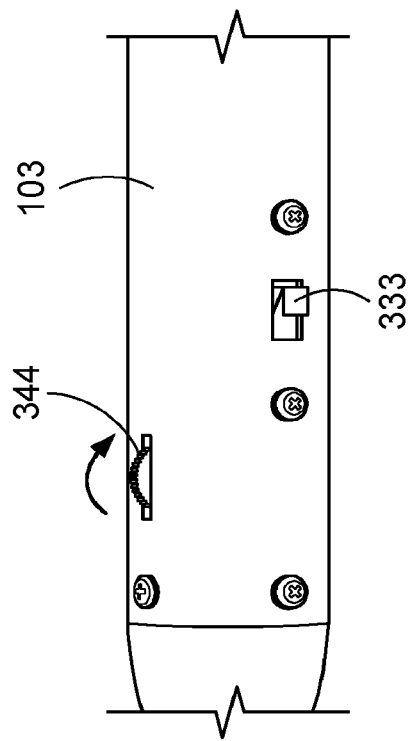
FIGS. 3A-3D illustrate a primary treatment probe in various treatment positions and intensity levels.
Figure 3B:
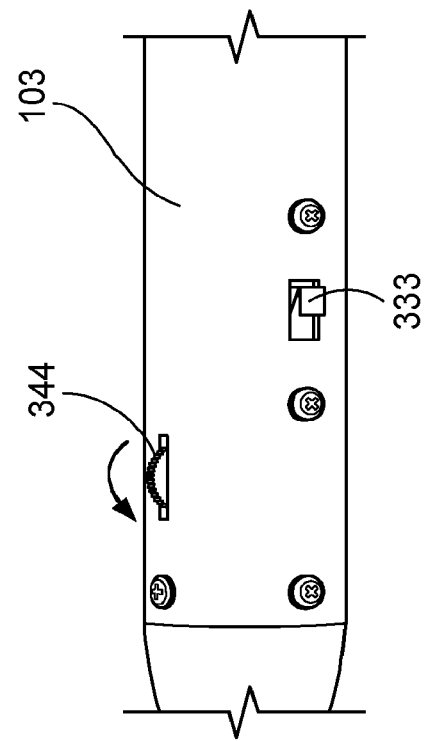
Figure 3C:
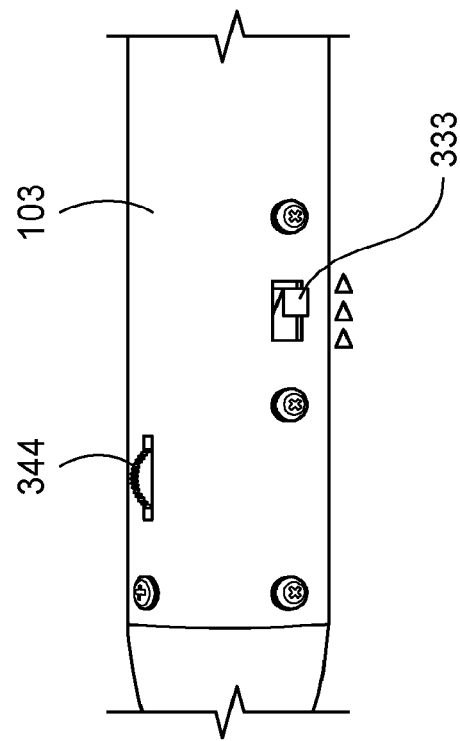
Figure 3D:
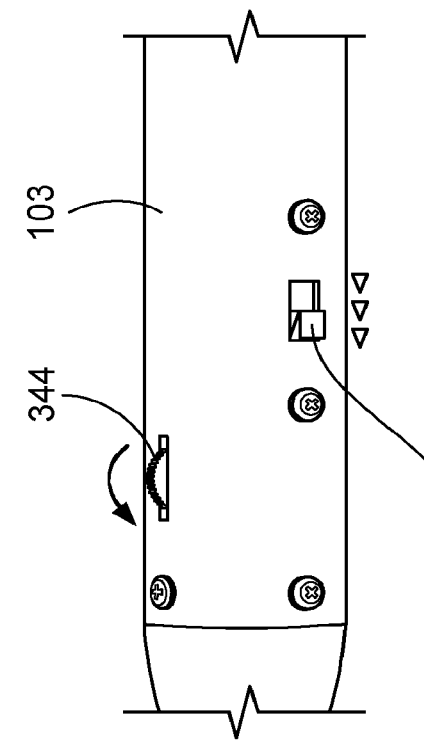

The primary probe 103 includes a treatment switch 333 shown in FIGS. 3A-3D that, when in a back position as shown in FIG. 3A, reads the relative conductivity between primary probe 103 and secondary probe 105 in a "measurement" mode. In the measurement mode, a small amplitude current is applied between the probes 103 and 105 to measure the impedance of the tissue to be examined. Voltage and current may be sensed and measured on a cycle by cycle basis, and impedance readings are calculated on a cycle by cycle basis. In measurement mode, the treatment switch 333 activates the contact level display 214 in FIG. 2 to provide a visual indication of the conductivity and impedance of the tissue under examination. When pushed forward as shown in FIG. 3B, the treatment switch 333 activates treatment by completing the coils sense circuit 117 that enables the probe stimulus generator 101 to generate an electrical pulse train output to treat the tissue under examination. When switched to treatment mode, the probe stimulus generator 101 receives a handshake signal from the treatment counter circuit 115. In this fashion, probe stimulus generator 101 may provide output current to the probes 103 and 105 in the form of the electrical pulse train when the treatment counter circuit 115 is in the circuit. The probe stimulus generator 101 also checks the power supply circuit 121 to ensure that proper power is provided prior to enabling output current in the form of an electrical pulse train. If the power is not adequate, or if the treatment counter circuit 115 does not shake hands, the stimulus generator 101 is prevented from outputting the electrical pulse train. The various handshake checks are made by a handshake controller. When the patient treatment unit 100 is in the treatment mode, the impedance between the probes (and therefore the impedance of the tissue under examination) is shown in the contact level display 214 in FIG. 2. The LED indication in the contact level display 214 in FIG. 2 remains on during the measurement modes. Additionally, the primary probe 103 includes an intensity dial 344 shown in FIG. 3B that controls the intensity of treatment. At the onset of treatment, the intensity dial 344 should be turned toward the back of the probe at its minimum setting as shown in FIG. 3B. The intensity dial 344 is then turned forward toward the front of the probe 103 as shown in FIG. 3C-3D until the patient feels the carrier current, but is not uncomfortable.

The body impedance analysis circuit 107 senses voltage and current via the probes 103 and 105 when the probes 103 and 105 are contacting the patient. The sensed voltage and current provide a means to measure the impedance of the examined tissue and to vary the position of the applied electrical pulse train, the frequency of the pulse train, the pulse width, the carrier current, and the like. As indicated above with regard to the probe stimulus generator 101, by setting an accurate frequency, amplitude, and pulse width of the electrical pulse waveform, the body impedance analysis circuit is better able to determine an accurate impedance measurement of the examined tissue. Changes in impedance may then be measured causally based upon the applied treatment rather than ascribed to any drift in the carrier waveform frequency or electrical noise.

As shown in FIG. 1, the monitor circuit 109 is electrically coupled to the body impedance analysis circuit 107 and provides an audio, visual, or other indication of the impedance, the sensed voltage, or the sensed current indicative of the patient's level of pain. The body impedance analysis circuit 107 may also simultaneously sense voltage and current associated with skin and tissue measurements as well as convert sensed readings to characterize other properties of the measured tissue such as conductivity, impedance, and the like. The indication may be provided by the speaker 111, an external display 140, or another indicator. In this fashion, the body impedance analysis circuit 107 may be used to measure surface and tissue impedance of the patient using the sensed voltage or current from the probes 103 and 105 and indicated to a physician or other operator. The body impedance analysis circuit 107 may also be used to measure the electrical phase of the voltage and current sensed from the probes 103 and 105 and may include a filtering circuit 113 in which waveform ripples in the sensed voltage or current are corrected. The display driver 135 may be used to illuminate LEDs 137 and 139 which form the contact level display 214 to provide an indication of the sensitivity of the probe measurement. Of course, other visual or audio methods of indication may be used as well. The monitor circuit 109 may include an audio output to speaker 111 that includes a frequency cut off volume to provide an indication of the sensed voltage or current or a visual indication of the determined impedance.

The treatment counter circuit 115 detects and tracks an elapsed treatment time indicative of the time the primary probe 103 is receiving the sequence of electrical pulses. The treatment counter circuit 115 may be used to measure and track treatments for regulatory and insurance compliance and to ensure patient safety. A visual indication of the treatment time may be presented using the display circuit 133 which drives the algorithmic evaluation code display 216 in FIG. 2. Patient compliance with treatment is a medical concern regardless of the form of treatment. Patients must follow through with the prescribed treatments to ensure efficacy and to facilitate recovery. If a patient avoids treatment or takes part in the treatment in a manner not prescribed, the patient's noncompliance masks any effects of the treatment. This leads to great uncertainty as to the effectiveness of the prescribed therapy and whether the current level of treatment is appropriate, or if it is in need of adjustment or discontinuation. Patients are often unwilling to admit they are non-compliant, and when a treatment is difficult or painful, patients may choose to forgo or avoid the treatment despite proven therapeutic benefits. Misuse of the treatment weakens the economic and therapeutic incentives for health care providers and insurance companies to fund or cover the costs of the treatment.

To ensure compliance for both medical outcomes and insurance requirements, the patient treatment unit 100 includes the algorithmic evaluation code display 216 as a compliance monitoring tool as shown in FIG. 2. The algorithmic evaluation code display 216 tracks and displays the treatment time during which an electrical pulse train is applied to the affected patient tissues. The algorithmic evaluation code (treatment) counter 115 runs continuously as long as the patient treatment unit 100 is in treatment mode and thereby tracks actual treatment time. Each time the patient treatment unit 100 is powered on, the current software revision will be illuminated in the algorithmic evaluation code field display 216. The software version number remains illuminated until the patient treatment unit 100 is turned off or until the treatment is activated by pushing forward the treatment switch 333 on the primary probe 103 as shown in FIGS. 3A-3D and described below with regard to FIGS. 6A-6B. Once the treatment switch 333 is activated and treatment begins, the treatment counter circuit 115 will take over the algorithmic evaluation code display 216, and the code display 216 will track the timed elapsed via a hexadecimal display or other indicator. The algorithmic evaluation code display 216 will continue to count as long as the primary probe 103 remains in treatment mode. Once the treatment switch 333 is deactivated (that is, the patient treatment unit is returned to the measurement mode), the algorithmic evaluation code 216 will stop incrementing but will remain visible. Algorithmic evaluation code display 216 will not increment until the treatment switch 333 on primary probe 103 is once again moved forward to re-start additional treatment. At that time, the algorithmic evaluation code display 216 will again continue to increment. With each patient treatment session, the starting value for algorithmic evaluation code display 216 must be noted upon commencement of the treatment session and at the end of the treatment session, the end value on the algorithmic evaluation code display 216 must be noted. These values should be recorded in the patient's file to track treatment times and compliance. Of course, these values may be recorded electronically and stored in a memory device.

Returning to FIG. 1, the coils sense circuit 117 is an option that evaluates the presence of a probe connection and enables the probe stimulus generator 101 when the probes 103, 105 are connected to the body impedance analysis circuit 107. The coils sense circuit 117 ensures that no electrical pulse train is generated when the probes 103, 105 are not properly connected.

The wall wart power supply 119 and the power supply circuit 121 provides a stable and regulated 12 volt DC power source to the patient treatment unit 100 in this example. The stable and regulated power source helps provide an electrical pulse train free from ambient electrical noise. Further, the patient treatment unit employing a wall wart power supply 119 and power supply 121 is less susceptible to fluctuations in AC input power typically provided by convenience outlets and other conventional power receptacles. The wall wart power supply 119 and power supply circuit 121 promote treatment efficacy and lower treatment costs by eliminating the need to replace batteries during treatment or at other inopportune times as may be the case with conventional systems.

Likewise, the wall wart power supply 119 and power supply circuit 121 eliminates the need to monitor battery power and to make adjustments to power output once the overall power level of the battery source has dropped beneath a threshold power level. By employing the wall wart power supply 119 and power supply circuit 121, the output signal (electrical pulse train) of the patient treatment unit is less susceptible to fluctuations following power disruptions, defective operations, or operator misuse.

The programming and debugging circuit 123 is used to configure the patient treatment unit 100 and to debug processing errors in the patient treatment unit 100. The programming and debugging circuit 123 may be integral hardware to the patient treatment unit 100 or may be deployed via the external input/output connection 125 to accommodate a laptop computer or other device that may provide input commands and receive output commands to program, analyze, and process computer instructions used to carry out different methods using the patient treatment unit 100. The programming and debugging circuit 123 may also be used to update the computer program instructions used to carry out a method of the present invention.

The treatment area selection circuit 127 is used to select a narrow treatment area using a "polarity" setting, or a diffused treatment area using a "reverse polarity" treatment area setting. By toggling between modes, the polarity of the pulse train created between the primary and the secondary probes 103 and 105 is reversed. The electrical pulse train may then be applied to the selected affected treatment area in a narrow space or in a wider physical space via the probes 103 and 105.

The response level circuit 131 is used to measure and indicate the conductivity or impedance between the probes 103 and 105. The intensity adjustment circuit 129 is used to measure, indicate, and adjust the intensity of the electrical pulses. The intensity of the electrical pulses may be varied by adjusting a carrier current or the pulse width of the electrical pulse train using the intensity dial 344 shown in FIG. 3D.

Figure 4:
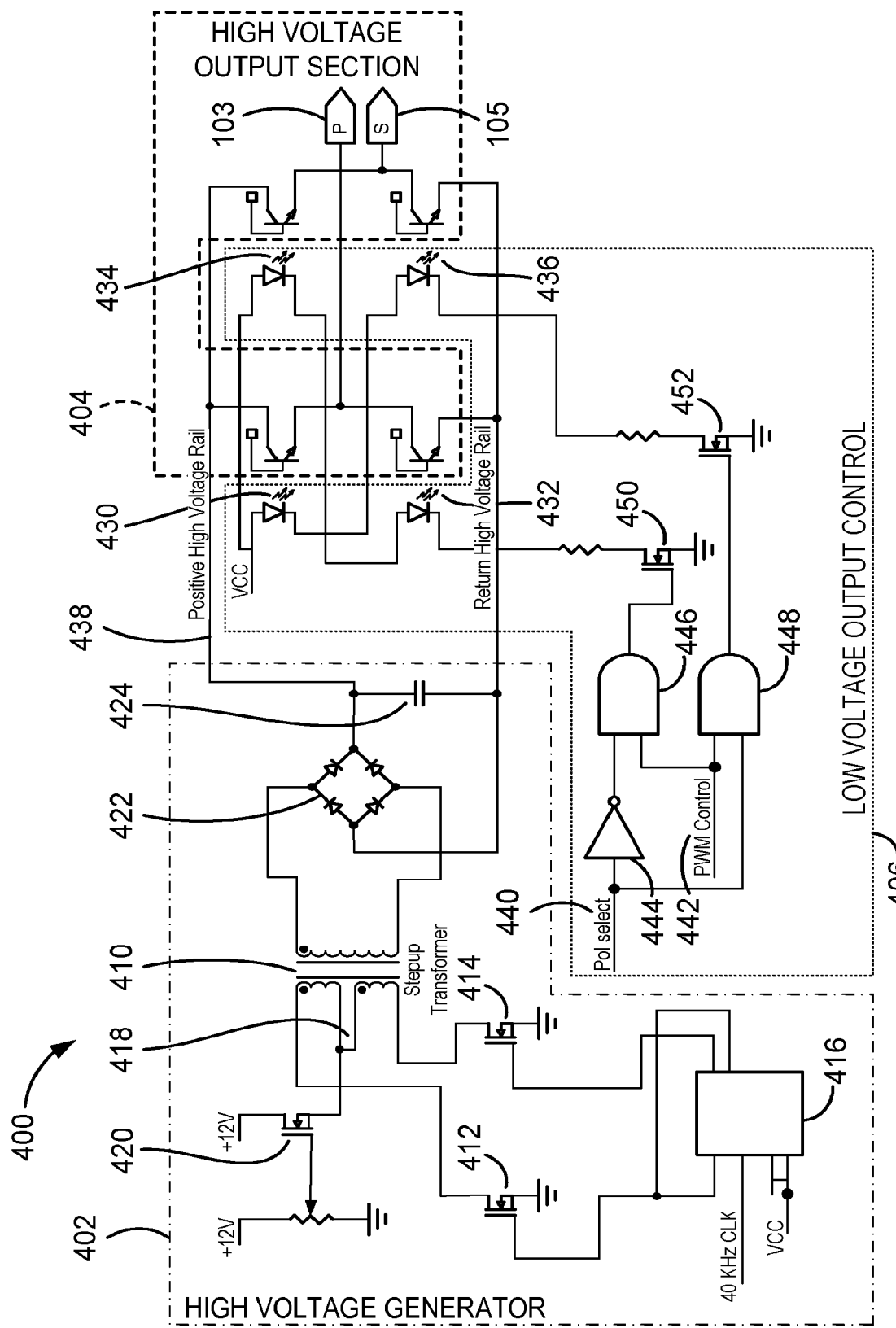
FIG. 4 is a circuit diagram of the waveform generator of the patient treatment unit of FIG. 1.

FIG. 4 is an example pulse forming circuit 400 that isolates the high voltage for the probes 103 and 105 that may be included in the probe stimulus generator 101. The pulse forming circuit 400 isolates high voltage from the lower voltage control circuits to produce a cleaner waveform with better pulse shape free of ringing. The resulting uni-polar waveform output promotes uni-directional ionic flow, creating a better net effect. The pulse forming circuit 400 includes a high voltage generator 402, a high voltage output circuit 404 and a low voltage output control circuit 406.

The high voltage generator 402 includes a step up transformer 410, a set of MOSFETs 412 and 414 and a D flip flop 416. A center tap input 418 is coupled to a control MOSFET 420 that is coupled to a DC voltage source such as the power supply circuit 121. The secondary coil of the transformer 410 is coupled to the inputs of a rectifier bridge 422. The outputs of the rectifier bridge 422 are coupled to a capacitor 424. The high voltage that will be applied to the body is created by the transformer 410 and then rectified by the bridge 422 and stored on the capacitor 424. The transformer 410 in this example is relatively small and is driven by the push-pull circuit configuration composed of the primary coil of the transformer 410, the MOSFETs 412 and 414 and the D flip flop 416 which is driven by a 40 kHz clock input. A higher clock frequency allows a smaller transformer to be used. The output voltage from the high voltage generator 402 is a function of the center tap voltage coupled to the control MOSFET 420 and the turns ratio of the transformer windings (primary to secondary turns).

In this example the output voltage is applied to the probes 103 and 105 by the use of high voltage opto-isolators 430, 432, 434 and 436. Either the combination of opto-isolators 430 and 436 are used to output voltage to the probes 103 and 105 respectively, or to reverse the polarity, opto-isolators 432 and 434 are used to output voltage to the probes 103 and 105 respectively. The output of the high voltage generator 402 is coupled to a positive high voltage rail 438 that is controlled by the high voltage ends of the opto-isolators 430, 432, 434 and 436.

The selection of the polarity of the output of the probe stimulus generator 101 is made via the low voltage output control circuit 406. The low voltage output control circuit 406 includes a polarity selection input 440 and a pulse width modulation control input 442. The low voltage output control circuit includes an inverter 444, AND gates 446 and 448, and output MOSFETs 450 and 452. The output MOSFET 450 controls activation of the low voltage end of the opto-isolators 432 and 434 while the output MOSFET 452 controls activation of the low voltage end of the opto-isolators 430 and 436. The polarity selection signal is received via the selection input 440 and is directly coupled to one input of the AND gate 446 and via the inverter 444 to one input of the AND gate 448. The output of the AND gates 446 and 448 drive the MOSFETs 450 and 452 respectively. The other input of the AND gates 446 and 448 are driven by a pulse width modulation control signal from the control input 442. The pulse width control signal will time how long the output pulse is and at what frequency it is applied. Since the polarity selection signal is inverted to the AND gate 446, only one set of opto-isolators 430 and 436 or 432 and 434 are activated to control high voltage output to the probes 103 and 105. The opto-isolation of the low voltage control from the high voltage provides a cleaner pulse shape output. The transformer parameters do not limit stimulation frequency or pulse width in this circuit configuration.

The electrical output specifications of the example patient treatment unit 100 are shown below in Table 1:

TABLE 1

| | |
|---|---|
| Power Supply | 115 VAC, 60 Hz |
| | 12 volt, DC output |
| Maximum Power Consumption | 21 W |
| Output voltage | Range of normal use: 50-60 V |
| | Peak pulse amplitude: 190 V |
| Pulse Rate | 1-490 Pulses/second, ±6% or 4 kHz-20 kHz |
| Pulse Duration | 10-11 microseconds |
| Output Current (maximum) | 8.9 milliamps |
| Maximum charge per pulse | 7 micro coulombs |
| Wave Form | Complex pulse trains: variable frequency, variable pulse width, AC-coupled rectangular pulse |

FIGS. 5A-5D show output waveforms of a patient treatment unit 100 in accordance with the present invention. FIGS. 5A-5D illustrate a number of impedance, power, and frequency relationships. For example, FIG. 5A shows a frequency response using a 1 MΩ maximum impedance. The output waveform varies depending on the load as shown in FIGS. 5B-5D. That is, FIG. 5B shows voltage versus time at 500 ohms. FIG. 5C shows voltage versus time at 5 kΩ ohms, and FIG. 5D shows voltage versus time at 10 kΩ. Changes in load affect both pulse duration and maximum pulse frequency. For example, maximum pulse rate frequency is in a range of 490 Hz±6% from 500 ohms to 1 MΩ. Lower impedances have lower maximum pulse rates, while pulse width is fixed for a given impedance. For example, pulse width is 0.74 milliseconds at 500 ohms and is 0.24 milliseconds at 1 MΩ.

Figure 8:
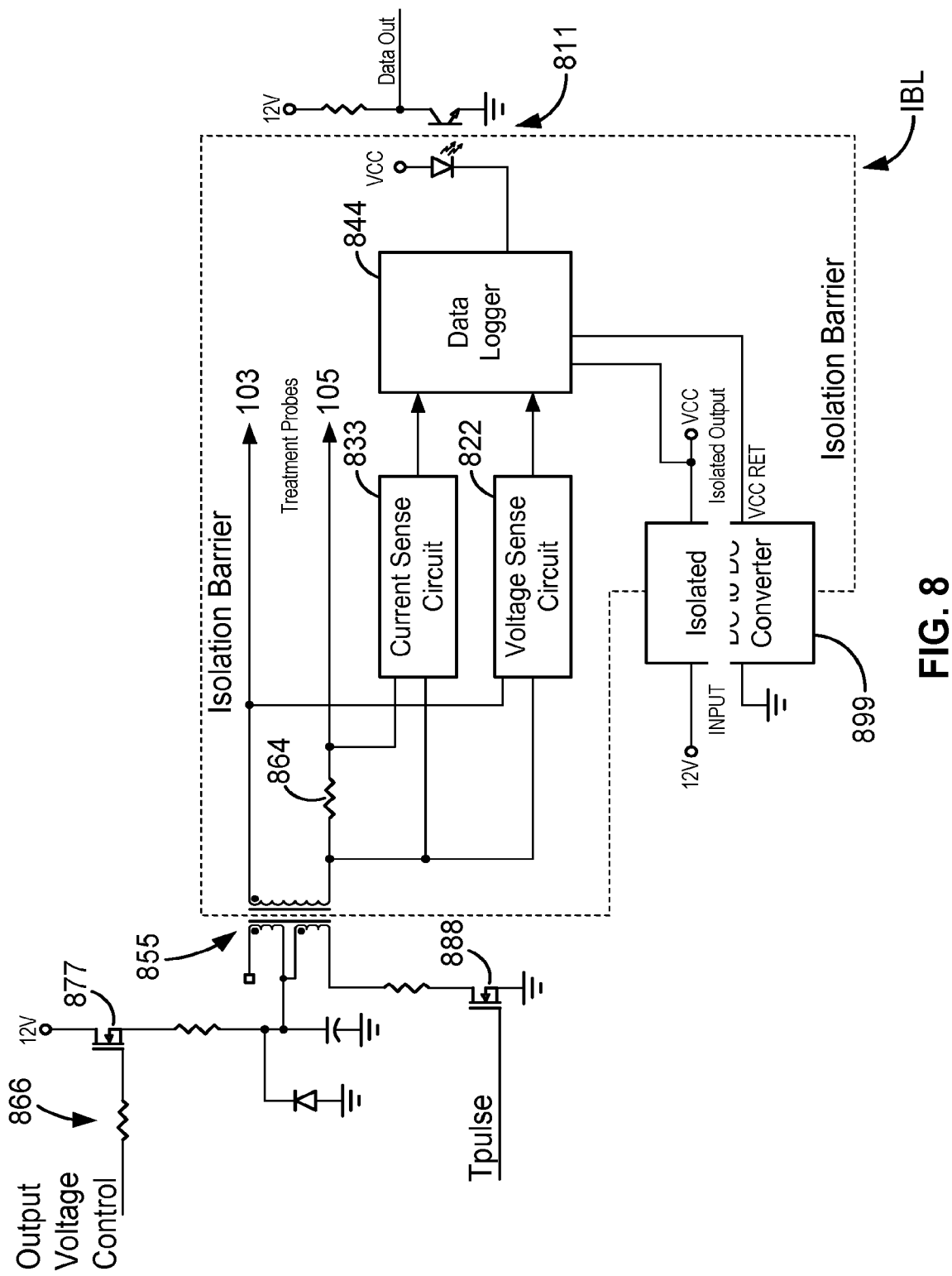
FIG. 8 is a block diagram of a measurement interface for real-time impedance and current measurements for the treatment unit in FIG. 1.

As further illustrated in FIG. 8, to measure impedance in real-time, a stimulation voltage is applied between the vibrating spherical probes 103 and 105 to measure the impedance of the tissue to be examined. The stimulation voltage is isolated from the pulse generator circuit of the probe stimulus generator by a transformer 855. As outlined above, any additional equipment or accessories that may be attached to the vibrating spherical probes or output circuit should be isolated from any circuit that could have a path to the AC mains, which includes the pulse generating circuit of the probe stimulus generator.

Voltage and current can be sensed and measured, and impedance readings are calculated. For example, the output pulse amplitude is controlled by the output voltage control input at a resistor 866 into the gate of a transistor 877. The pulse width and timing is controlled by a TPULSE input signal into a transistor 888. Besides isolating the pulse, the transformer 855 also serves to amplify the pulse from the 12 volt or less level to some much higher voltage determined by the turns ratio of transformer 855.

Anything within the isolation barrier line IBL is either galvanically or optically isolated so there will be no current passed over this barrier. Capacitive coupling may also be used to further isolate the current.

An isolated DC to DC converter 899 provides the isolated power to operate the data logger 844 electronics. A current sense circuit 833 senses the voltage across a low value resistor 864 to sense the current passing through the vibrating spherical probes 103 and 105. A voltage sense circuit 822 senses the voltage across the vibrating spherical probes 103 and 105. This sensed data is passed on to the data logger 844 circuit, which can either calculate the body impedance by dividing the sensed current into the sensed probe voltage, or pass on these parameters to other circuits where the calculation may be performed. As shown in FIG. 8, the data values are passed in this example as digitized data over an optically isolated serial bit stream through opto-isolator 811. The raw analog data can also be passed across this barrier by analog coupling schemes. As will be explained, this data can be presented to a user in a plotted format of impedance-versus-time to show the change in impedance value with treatment time for a particular probe placement.

Figure 7A:
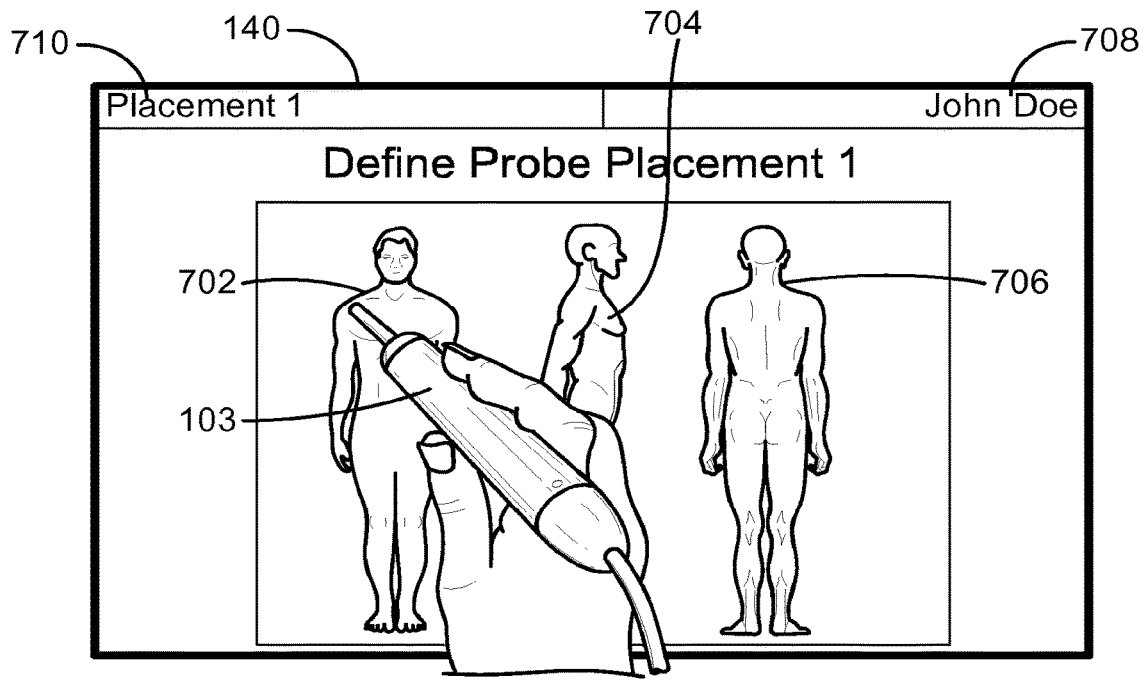
FIGS. 7A-7B are diagrams of a display interface used to assist in positioning probes from the patient treatment unit of FIG. 1 on the correct positions on a patient.
Figure 7B:
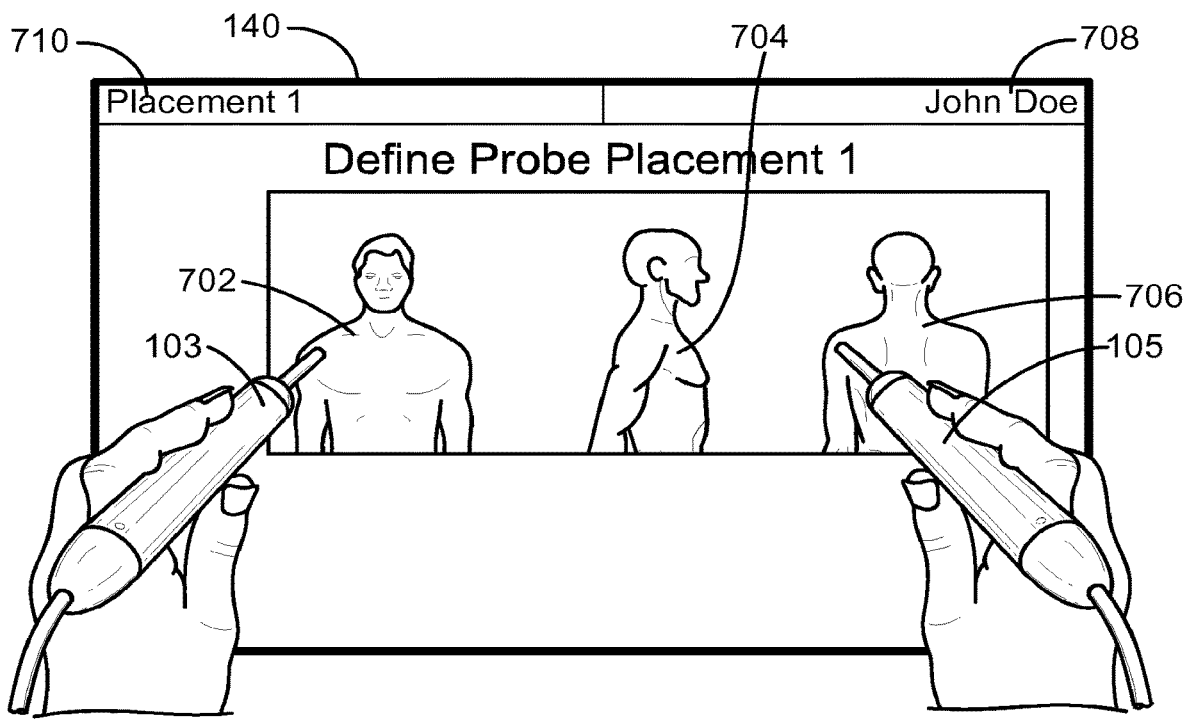
Figure 7C:
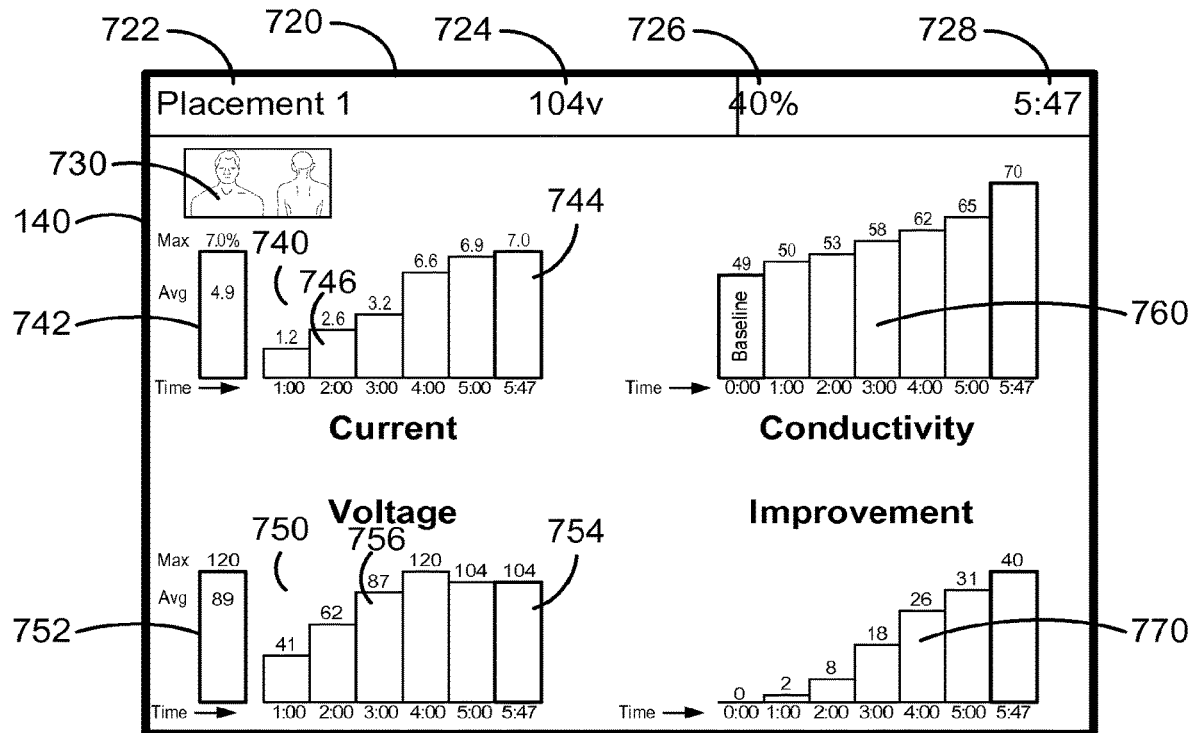
FIGS. 7C-7D are a screen shot of a graphic interface that displays real-time impedance data based on the probes from the patient treatment unit of FIG. 1.
Figure 7D:
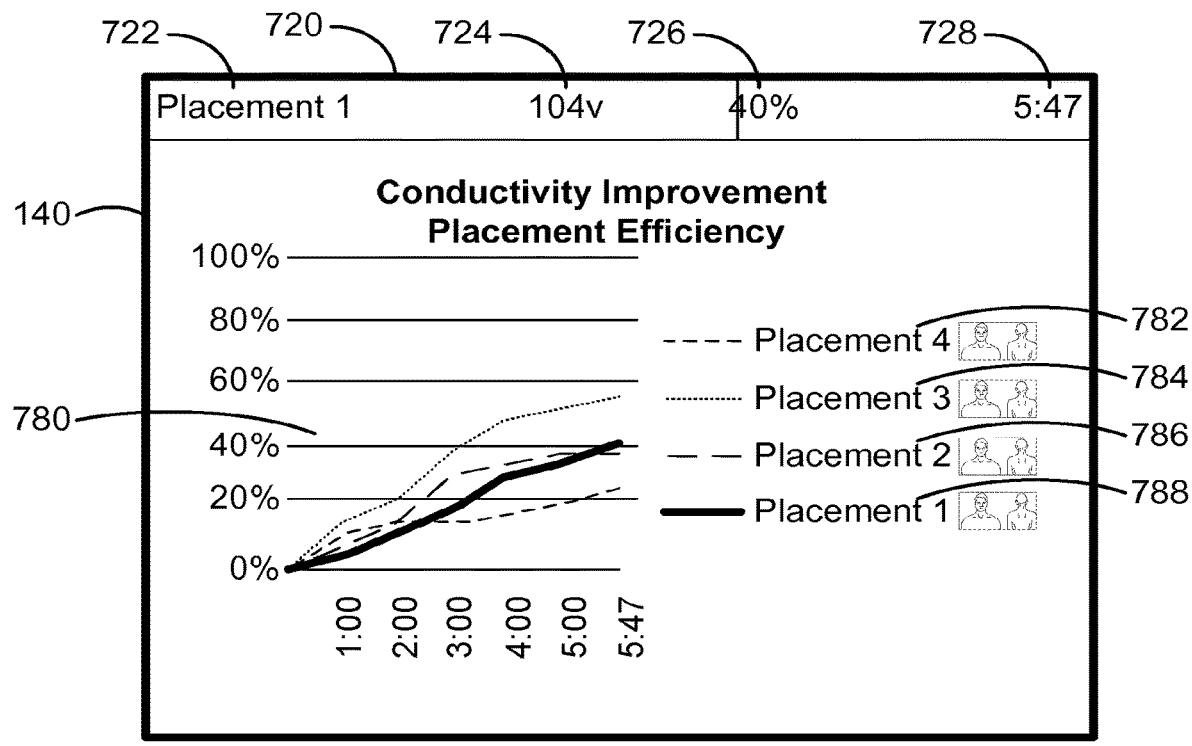

The isolated data logger circuit shown in FIG. 8 measures impedance on a cycle-by-cycle basis to provide real-time impedance output during the treatment mode. The placement of the probes initially may be assisted with graphics displayed on the video display 140. FIGS. 7A-7B show graphics with the use of the probes 103 and 105 to insure proper placement of the probes 103 and 105. The resulting real-time impedance output data may be displayed in a graphical user interface as shown in FIGS. 7C-7D.

FIG. 7A shows the display 140 with the probe 103. In this example, the display 140 has touch screen capabilities. The display 140 in FIG. 7A shows an initial screen to assist the user to placement of the probe 103. After inputting the patient's name and particulars, the screen image in FIG. 7A may be displayed for the user to input the placement of the probes such as the probe 103 shown in FIG. 7A. The user calls up a series of generic anatomical illustrations 702, 704 and 706 that show the front, side and back graphics of a patient body. The screen image in FIG. 7A includes a data field 708 that may include input data such as the patient name and other data that may be stored as explained above. A status field 710 includes information about the placement of the probes. In this example, each different placement of the probes 103 and 105 are termed "Placement 1," "Placement 2," etc.

A user of the patient treatment device in FIG. 1 would call up the screen graphic showing the generic anatomical illustrations 702, 704 and 706. The user would then use a probe tip of a probe such as the probe 103 on the touch screen of the display 140 to identify the general area to zoom in on at which "Placement 1" will be given. Once the probe tip is used to trigger the zoom in function, then the screen would zoom in to the selected area as shown in the screen in FIG. 7B.

The screen in FIG. 7B includes enlarged versions of the anatomical illustrations 702, 704 and 706. The user may then use the actual primary probe 103 and the secondary probe 105 to precisely define the locations on the patient's body via the anatomical illustrations 702, 704 and 706 for the treatment in the Placement 1 position. The touch screen may distinguish the probe locations of the primary probe 103 from the secondary probe 105. The effectiveness of the treatment may be measured in real-time thus indicating that the treatment is effective if impedance is lowered. Impedance is measured by analyzing the voltage and current of the treatment waveform to determine body impedance instead of a separate DC voltage circuit. The data relating to real-time current values delivered to the patient may be stored. The isolation components in FIG. 8 may also be adapted for impedance measurements with other circuits for waveform generation such as that shown in FIG. 4.

Once the locations of the probes 103 and 105 are established, treatment using the treatment device in FIG. 1 begins. All of the measurement and feedback of the measurement is done in an isolated manner so as to prevent any possibility of harm to the patient by having inadvertent currents pass through the body. The only current passing through the body is supplied by the stimulation voltage and not the measurement circuitry. The data output of the data logger circuit in FIG. 8 may be stored and displayed for use by the clinician as shown in the display in FIGS. 7C-7D. The display of the data in FIGS. 7A-7D may be made on an external video display 140 in FIG. 1 or another display device. The optional user interface module 150 includes a storage device 151 with a database 153. A computing device 155 may run various software applications to display data to assist the clinician prior and during the application of the probes 103 and 105 of the treatment unit 100. The real-time graphical displays in FIGS. 7C-7D depicts the change of impedance versus time as the intensity, frequency, and/or polarity parameters are adjusted during treatment. The rate of change of impedance can also be calculated and displayed as a function of time.

As treatment commences, the graphics shown in FIG. 7C are displayed to provide the user real-time information about the treatment. The screen in FIG. 7C includes a data top line 720 which displays in large graphics the most important real-time data for the user. The data top line 720 includes a placement data field 722 which includes the placement position, a real time voltage output field 724 showing the real time voltage applied, a real-time improvement field 726 showing the real-time percent improvement in conductivity vs. the conductivity when the treatment in this placement began, and a clock field 728 showing the elapsed time of the treatment since this placement began. A location graphic 730 shows the area of the anatomy the probes are located. Each of the probes 103 and 105 are designated by a separate graphic such as "P" and "S" respectively in the location graphic 730.

FIG. 7C also includes a number of real-time data graphs 740, 750, 760 and 770. The graph 740 is a real-time current graph which includes a maximum bar 742 with a graphic showing the mean current. The maximum bar 742 thus reflects the maximum current actually delivered to the body once resistance is factored in and contains mean current information. The present voltage measurement is shown in a real-time bar 744 which also shows the present time after treatment has commenced. The graph 740 also includes bars 746 that reflect current actually delivered to the body once resistance is factored in as applied on a minute-by-minute basis. Of course other time units may be used to segment the bars 746.

The graph 750 is a real-time voltage graph which includes a maximum bar 752 with a graphic showing the mean voltage. The maximum bar 752 thus reflects the maximum voltage and contains mean voltage information. The present voltage measurement is shown in a real-time bar 754 which also shows the current time after treatment has commenced. The graph 750 also includes bars 756 that reflect voltage applied on a minute-by-minute basis. Of course other time units may be used to segment the bars 756.

The graph 760 shows various bars showing the conductivity first measured when the treatment is first applied and then the changes each minute as the treatment progresses. The graph 770 shows the percentage change (improvement) measured in conductivity that may be attributable to the treatment. The graph 770 therefore is a barometer of pain relief as a result of the treatment by the patient treatment device in FIG. 1.

Other data may be plotted and displayed similar to the graphs 740, 750, 760 and 770. For example, the first derivative of impedance (dZ/dT) could be plotted where the slope going lower at a faster pace would show a higher value and impedance going higher would show up as a negative value.

FIG. 7D shows an alternate screen including a historical graph 780 including the percentage of conductivity improvement for different placements. The placements are charted in the form of placement graphics 782, 784, 786 and 788 corresponding to each of the placements of probes attempted for treatment. Each of the placement graphics 782, 784, 786 and 788 include a graphic showing where the placement of the probes were for that treatment as well as a code to the graph 780 such as color, shape of line, etc. The graph 780 allows a comparison of all the Placement probe positions recorded in this treatment can be overlaid to see which was most effective in improving conductivity. In this example, the placement 3 is the most effective. Of course more or less than the four placements shown in FIG. 7D may be compared.

The graphical user interface (GUI) in FIGS. 7C-7D enables a clinician to understand at a glance the efficacy of a particular combination of parameters on the body impedance. The graphics in FIGS. 7C-7D are plotted from the data obtained from the data logger circuit in FIG. 8. The information is in the most usable form for the clinician.

Further feedback may be in the form of voice message played over the speaker 111 in FIG. 1 reflective of the data shown in FIG. 5. Such voice audio feedback may be played using software on the computing device 155 so that the clinician can hear voice audio cues as to efficacy of treatment without having to keep eyes on the video display 140 or other displays. This enables a clinician to focus on a patient's subjective response instead of focusing on device. Tones are sometimes annoying to the patient and it has been noted that some clinicians turn down the volume because they also find the sounds annoying and distracting. By using a voice output that can be chosen for calming effect, the annoyance factor can be removed. Additionally, voice feedback has the capability to pass on much more information such as descriptions of different conditions or instructions.

Figure 9:
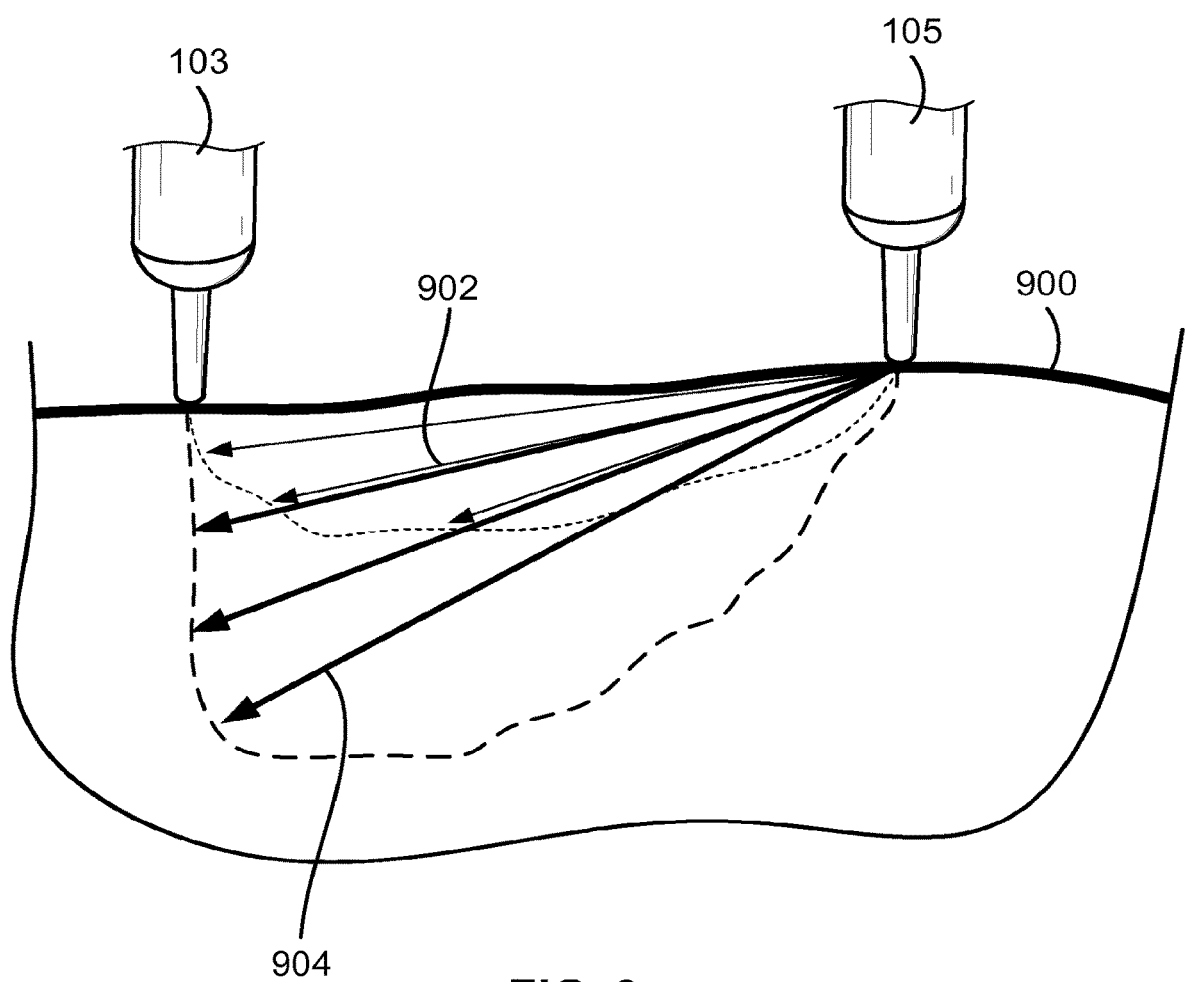
FIG. 9 is a cross section view of a patient and the probes of the patient treatment unit of FIG. 1.

FIG. 9 shows a cross section of the probes 103 and 105 in relation to patient tissue 900 to show an optional process to determine how deeply the current may be penetrating the tissue. The patient treatment unit 100 may track how long it takes for the current to arrive at the secondary probe 105 after leaving the primary probe 103 to provide an indication as to how deeply the current is penetrating the tissue 900. Electric current travels about an inch every 24 billionth of a second. If there is a differential distance between the surface current and the sub-surface current of ¼ where the probes 103 and 105 are 1" apart, it would take 6 billionth of a second for the current to arrive at the secondary probe 105.

The depth of penetration of current passing between two probes 103 and 105 using the human body as a conducting path may be determined on a relative basis by measuring current passed between the probes 103 and 105. The initial penetration is shallow as seen by initial current paths 902. As penetration is conducted deeper within the body tissue as shown by the current paths 904, it encounters more ionic body fluids that are more conductive. By varying frequency and simultaneously measuring the current as frequency is varied, the patient treatment unit 100 may measure the depth of penetration of current through the body tissue.

Returning the FIG. 1, the interface module 150 may include options for additional graphics for the external video display 140. For example, a graphic may be selected to show automated suggested probe starting points. Guided, malady-specific, treatment starting points will be indicated graphically on the external video display 140 to the clinician by consulting an internal database of maladies and their associated starting points for treatment. Such a database 153 may be stored locally on the storage device 151.

The database 153 may be managed by management software run on the computing device 155. Of course the functions of the computing device 155 may be performed on board the treatment unit 100 with appropriate hardware or remotely via a network. On the first visit a patient's malady may be entered and on subsequent visits when the patients name is entered on the computing device 155. The database 153 may provide a match with the patient and the relevant data such as the malady associated with that patient may be displayed on the video display 140. This data enables starting the clinician with the proper treatment suggestions and even show what was the most effective treatment was from the previous session.

Guidance may be given via visual cues with pictures showing where probes should be placed as explained above as well as audio suggestions on the video display 140. A graph of conductivity improvements showing the best improvement with probe placement and intensity setting (frequency, pulse width settings also) could be shown on the video display 140 when the patient's records are found and displayed from the database 153.

Figure 10A:
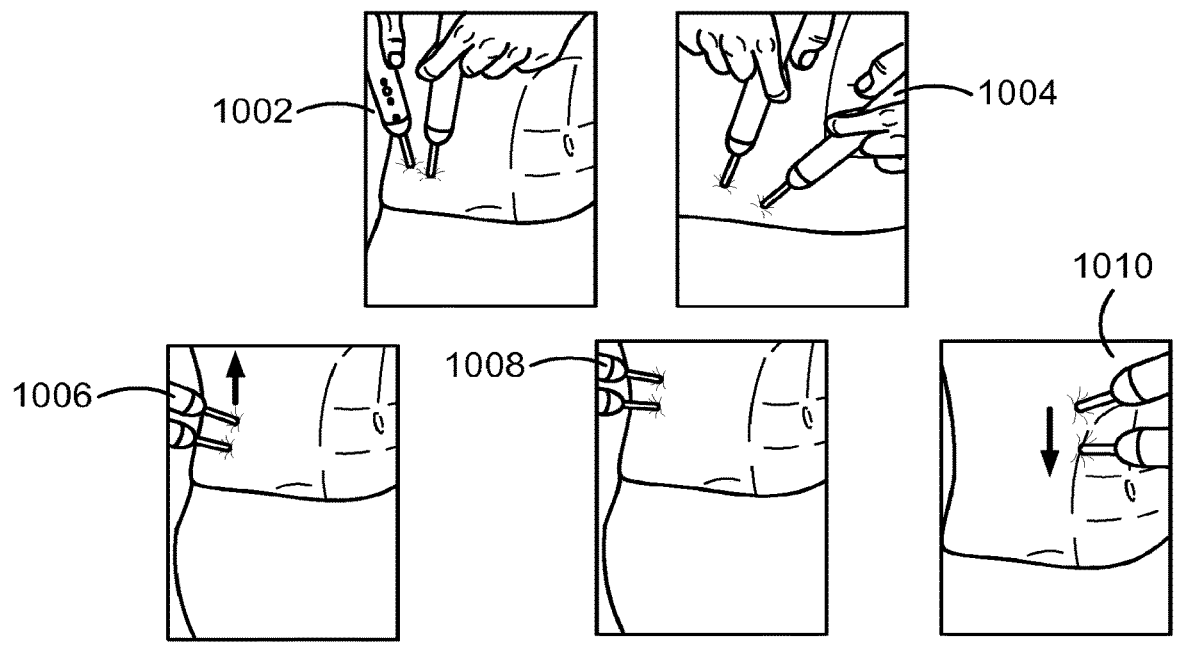
FIGS. 10A-10B are graphics displayed to assist the placement of probes for various treatments for the treatment unit in FIG. 1.
Figure 10B:
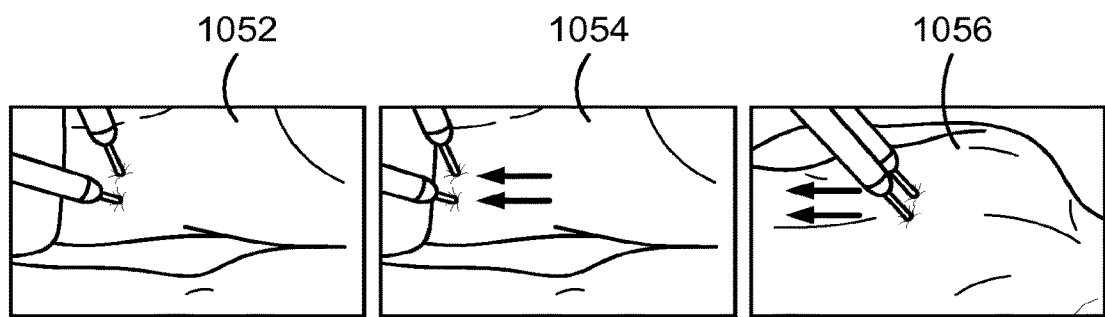

FIGS. 10A and 10B are examples of instruction graphics that may be displayed on the display 140 in FIG. 1. FIG. 10A includes five images 1002, 1004, 1006, 1008 and 1010 that are all indicative of treatment of a single symptom on the torso. The images 1002, 1004, 1006, 1008 and 1010 show the sequence of treatment using the treatment unit 100 in FIG. 1 and the placement of the probes 103 and 105. FIG. 10B is another example that includes a series of graphics 1052, 1054 and 1056 that may be displayed on the display 140 that demonstrates a lower back cure. The graphics in FIGS. 10A-10B would thus be displayed prior to the display of the display in FIG. 7A to assist a user in applying the selected treatment. Such displays show that there are several steps to application of this treatment modality. Such graphics may also illustrate the need for moving probes during treatment to properly affect the cure and how the treatment should progress.

Alternatively, the location of the probes 103 and 105 may be tracked as they are applied to the human body by means of a computer vision system consisting of a set of cameras 159 as shown in FIG. 1 feeding a computer such as the computing device 155 running vision system software. The vision software digitizes the images it is fed and is capable of recognizing features and relative positions. Sets of unique dots may be applied to reference points on the patient body in the area of treatment. For example, in treating a hand malady, stick on dots may be placed on each knuckle and the bones protruding from the wrist. The vision system recognizes these dots as well as the probes 103 and 105 and records the coordinates of probe placement in relation to the patient's anatomy.

The vision system may also receive inputs from RF ranging devices rather than camera input. The dots may be small RF antenna structures and the probes 103 and 105 may each have their own RF signature so as to allow detection by the treatment unit 100.

An optional security module 157 may be coupled to the computing device 155 and the treatment unit 100 to control overall access and protect patient data in the database 153. In one example, expiring datakeys are sent to the clinician periodically (e.g. one per month). The datakeys will no longer work after the period of time. In this example, the clinician must return used datakeys in exchange for a new one that is good for another period of time. A returned datakey includes record patient number and associated treatment time and dates for determining how much to bill the clinician.

To ensure payment for use of the treatment unit 100, the security module 157 is installed as an integral part of the operation of the treatment unit 100 and the interface module 150. The datakey includes a key. Without the key of the datakey product, the security module 157 may render the treatment unit 100 inoperable. In this example, the datakey is shaped like a conventional key, but is plastic with metallic contacts. Internal to the datakey construction is a memory integrated circuit that has non-volatile storage. This memory will have usage information stored in it by the computing device 155 after reading data from the treatment unit 100. The operating system of the security module 157 accesses time and date information via a real time clock (RTC) that is integral to the circuit components of the patient treatment unit 100. In this example, on a monthly basis the operating system will request a fresh key to be inserted in the computing device 155 to continue operation. In a lease arrangement, after inserting a new key that has been previously provided by the leasor, the leasee of the machine sends the used key back to the company after which the leasor shall send a fresh key for the subsequent month.

The used key received by the leasor has a record which contains sufficient information to provide billing information on usage of the patient treatment unit 100. Such information might be number of patients, time spent on treating each patient, total usage time, dates and time of each treatment, etc. that may be taken from the database 153.

The computing device of the interface module 150 may be used in conjunction with the patient treatment unit 100 to facilitate medical reporting. Sample data may be temporarily stored in the patient treatment unit 100 or the database 153 or elsewhere. This data may include (1) areas treated as inputted by clinician; (2) patient number; (3) patient's subjective rating of pain at beginning of session as inputted by clinician; (4) patient's subjective rating of pain (or lack thereof) at end of session as inputted by clinician; (5) total elapsed treatment time (6) objective data showing impedance change as a function of treatment. The computing device 155 may be attached to a printer to print out a record indicating the foregoing for attachment to the patient's medical record or for use as supportive attachments to billing forms. The data from the database 153 may also be uploaded by any of the common electronics means (wireless, wired, etc.). Other relevant clinical data such as range of motion etc. may also be included and made accessible to the clinician via the interface module 150.

Figure 6A:
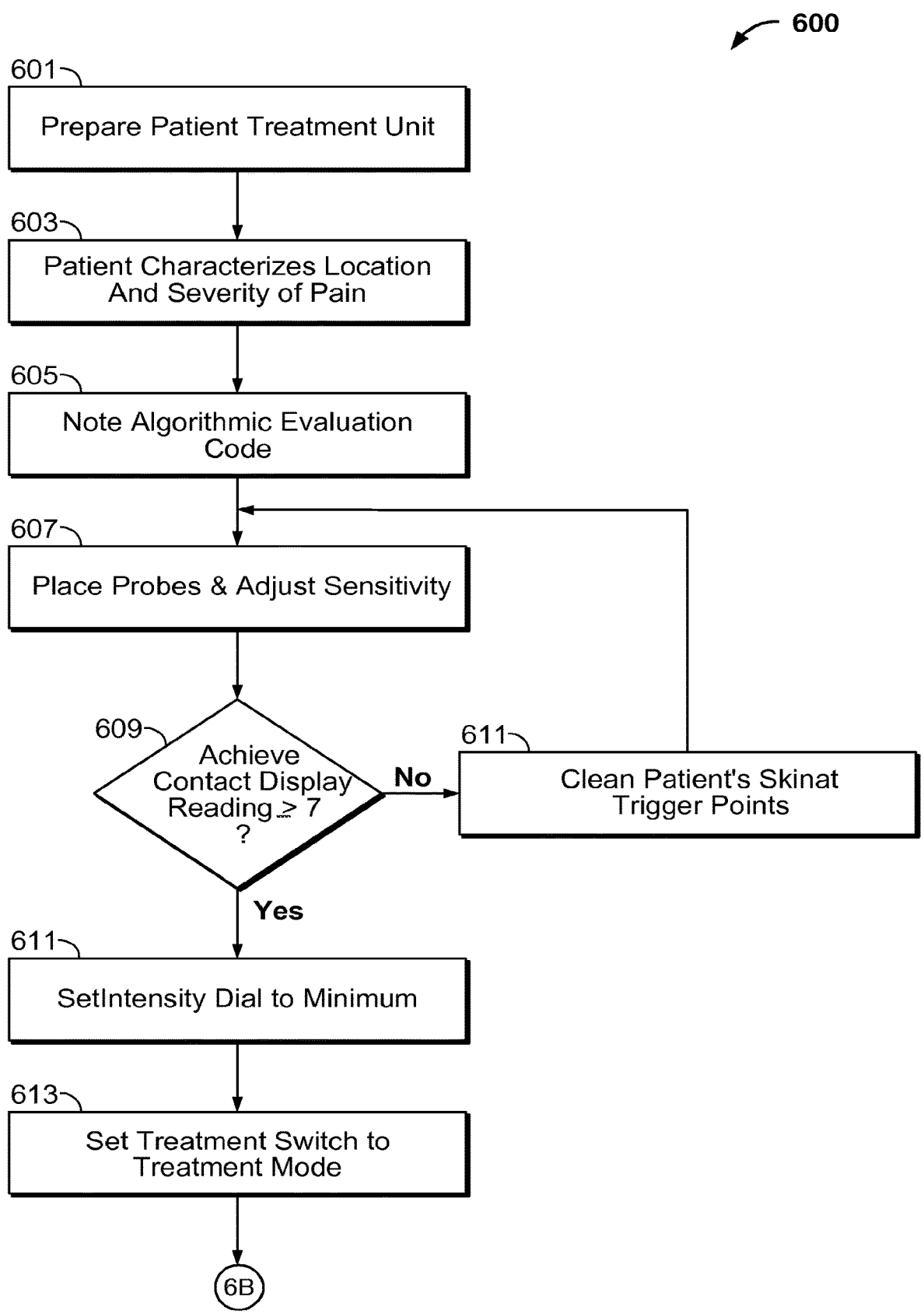
FIGS. 6A-6B are process flow diagrams outlining a method of analyzing and treating pain using a patient treatment unit.
Figure 6B:
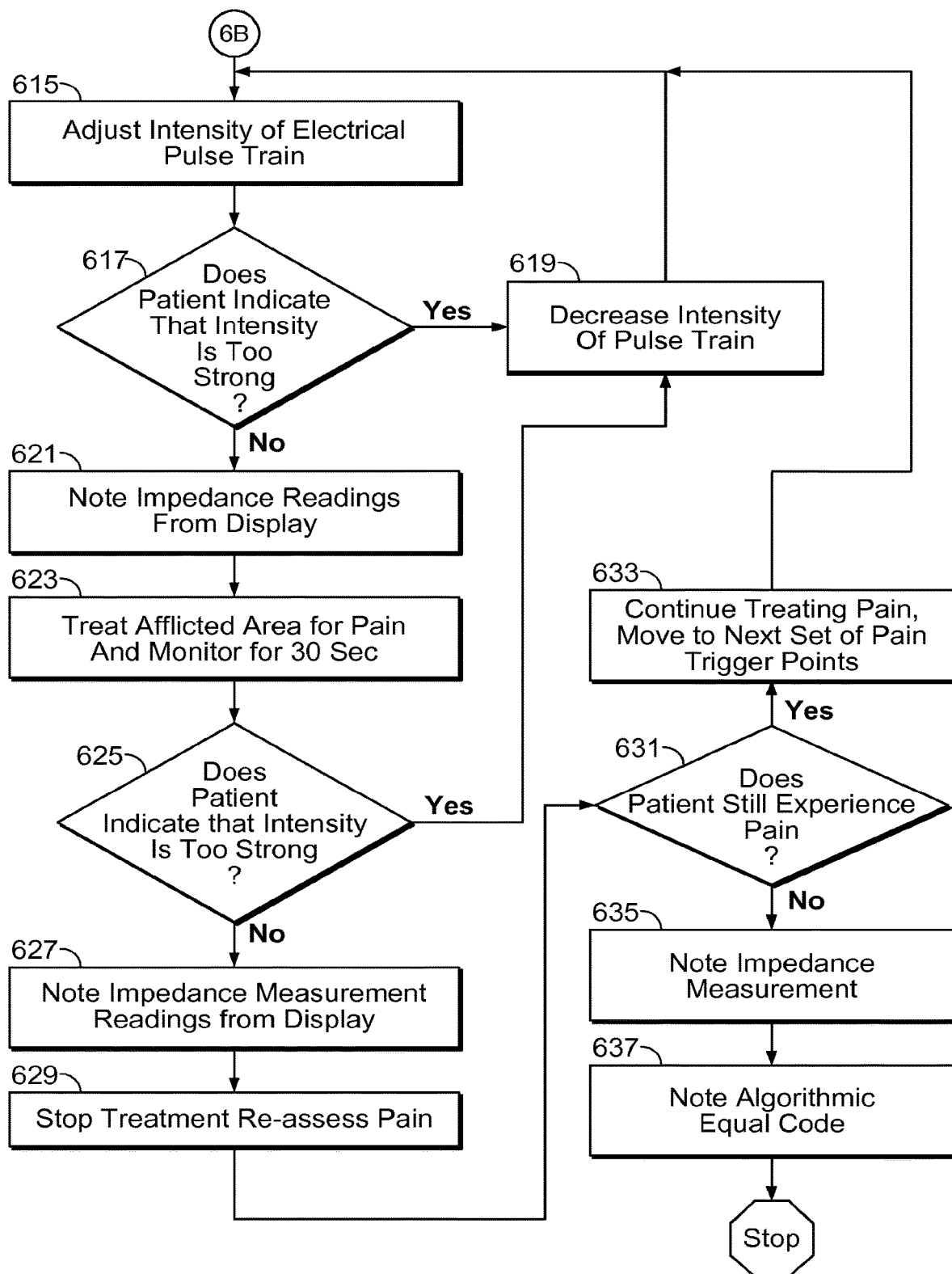

FIGS. 6A-6C illustrate a method 600 to control pain using a patient treatment unit 100 in accordance with the present invention. In step 601, a physician or other licensed operator makes the patient treatment unit 100 ready for use by preparing the initial device settings. As illustrated in FIG. 2, the initial device settings include the volume, tone, intensity, sensitivity, tone cut-off, and carrier. The volume knob 202 is used to adjust the volume of the sound indicators from monitor circuit 109. The tone knob 204 adjusts the frequency of an audible tone that is used to communicate the level of conductivity between the probes to ensure proper probe contact with the patient's skin. The intensity knob 206 controls the carrier voltage. The sensitivity/baseline calibration knob 212 adjusts the conductivity of the patient treatment unit. The tone cut-off knob 210 adjusts the response level at which an auditory signal will be heard. The carrier knob 208 controls the frequency of the carrier wave. Initially, the volume knob 202 is set to level of 5, and tone knob 204 is set to a level of 0. Additionally, the intensity knob 206 is set to a level of 10, and the sensitivity/baseline calibration knob 212 is set to a level of 5. Likewise, the tone cutoff knob 210 is set to a level of 0, and the carrier knob 208 is set to a level of 10. The frequency selector switch 219 controls whether the pulses outputted by the probes are low frequency (e.g., between 1 and 490 Hz) or high frequency (e.g., between 4 kHz and 20 kHz).

Returning to FIG. 6A, in step 601 the pain is characterized. For example, in conjunction with a patient history and examination results, the patient may characterize the location and severity of the pain. The patient may describe his or her pain in order to determine the scope and size of the problem and to establish a baseline measure of the perceived pain. The patient may point out the precise location of the most intense source of discomfort. For example, the patient may use a single finger to point at and touch the exact center of the pain point. Similarly, the physician may palpate the general area until the patient confirms the exact location of the most intense pain-related trigger point. The physician may continue to palpate the area to find a secondary trigger point. Once the location of the pain is identified and characterized, in step 605 the physician notes the displayed algorithmic evaluation code on the display 216 prior to beginning the treatment as discussed above and shown in FIG. 2.

Impedance readings are used to determine the condition of the tissue under examination. A reduction in impedance during or after treatment indicates the treatment is reducing the level of pain perceived by the patient. The patient treatment unit of the present invention makes impedance readings in the measurement mode. Periodically during treatment, the probes are switched from treatment mode to measurement mode to determine the effectiveness of the treatment. If the impedance measurement is lower than the initial measure, the treatment is effective. If the periodic impedance measurements are not lower during treatment, treatment may be continued. Additionally, the patient treatment unit of the present invention may be configured to regularly switch to measurement mode during treatment to provide an on-going, periodic display of the tissue impedance.

In step 607, the physician ensures that primary treatment probe 103 is set to the "measurement" mode, where the treatment switch 333 is placed in the back position as shown in FIG. 3A. Additionally, the physician selects the polarity using the polarity button 218 shown in FIG. 2. The physician then places the primary treatment probe 103 on the primary pain-related trigger point and the secondary treatment probe 105 on the secondary pain-related trigger point and notes the reading on the contact level display 214 as also shown in FIG. 2. The physician then adjusts the sensitivity knob 212 until a reading of 7 is achieved on the contact level display 214. For example, a typical impedance measurement may be 20 kohms with gel.

In step 609, if a reading of 7 cannot be achieved initially, the contact between the patient's skin and the probes 103, 105 may be inadequate, and the physician may clean the patient's skin at the pain related trigger points in step 611. For example, the physician may clean the patient's skin with an isopropyl alcohol swab and return to step 607 to place the probes 103, 105 firmly into the patient's skin and, if a reading of 7 still cannot be achieved, the physician may move the probes to an adjacent point on the patient's skin where a contact display reading of 7 can be achieved.

Once a contact display reading of at least 7 is achieved, in step 611 the physician turns the probe intensity dial 344 fully toward the back of the probe 103 indicative of minimum intensity. In step 613, the physician pushes the treatment switch 333 forward on the primary treatment probe as shown in FIG. 3C to select the treatment mode.

In step 615, the physician begins to adjust the intensity dial 344 forward on the primary treatment probe 103 as shown in FIG. 3C. As indicated above, the intensity of the electrical pulse train may be controlled by increasing or decreasing the pulse width, or by increasing or decreasing the carrier current. As the physician gradually increases the intensity of the electrical pulse train, the physician monitors the patient until the patient begins to feel the carrier current. The carrier current may feel like a tingly, or prickly sensation.

In step 617, the physician asks the patient to indicate when the intensity is strong and may reach the point of discomfort. Although higher intensity provides further pain relief, the patient should not experience significant discomfort. In step 619, the physician incrementally reduces the intensity of the pulse train, and returns to step 615 to optimize the intensity of the pulse train to just before the point where the intensity level has reached the maximum intensity level in which the patient remains comfortable. In step 621, the physician notes the impedance measurement of the area to be treated. The treatment then continues in step 623 for approximately 30 seconds. It is possible during treatment that the patient will begin to feel the treatment more strongly. If this occurs in step 625, the physician may use the intensity dial 344 on the primary treatment probe 103 to reduce the intensity of the electrical pulse train to a comfortable level.

After treating the affected tissue area for approximately 30 seconds, in step 627, the physician notes the impedance measurement of the treated area. Once noted, the physician stops treatment in step 629 by pushing the treatment switch 333 back on the primary treatment probe 103 as shown in FIG. 3D to stop the treatment and to take the probe 103 out of treatment mode. The physician then asks the patient to reassess his or her pain.

If pain remains in step 631, the physician continues to treat the pain in step 633 and moves to the next set of pain trigger points and repeats steps 615 to 631. If the pain is remediated, or if the pain is insignificant after treatment, or if further progress in ameliorating the pain may not be made, the physician notes the impedance measurement in step 635, notes the algorithmic evaluation code in step 637, and ends the treatment.

Figure 11:
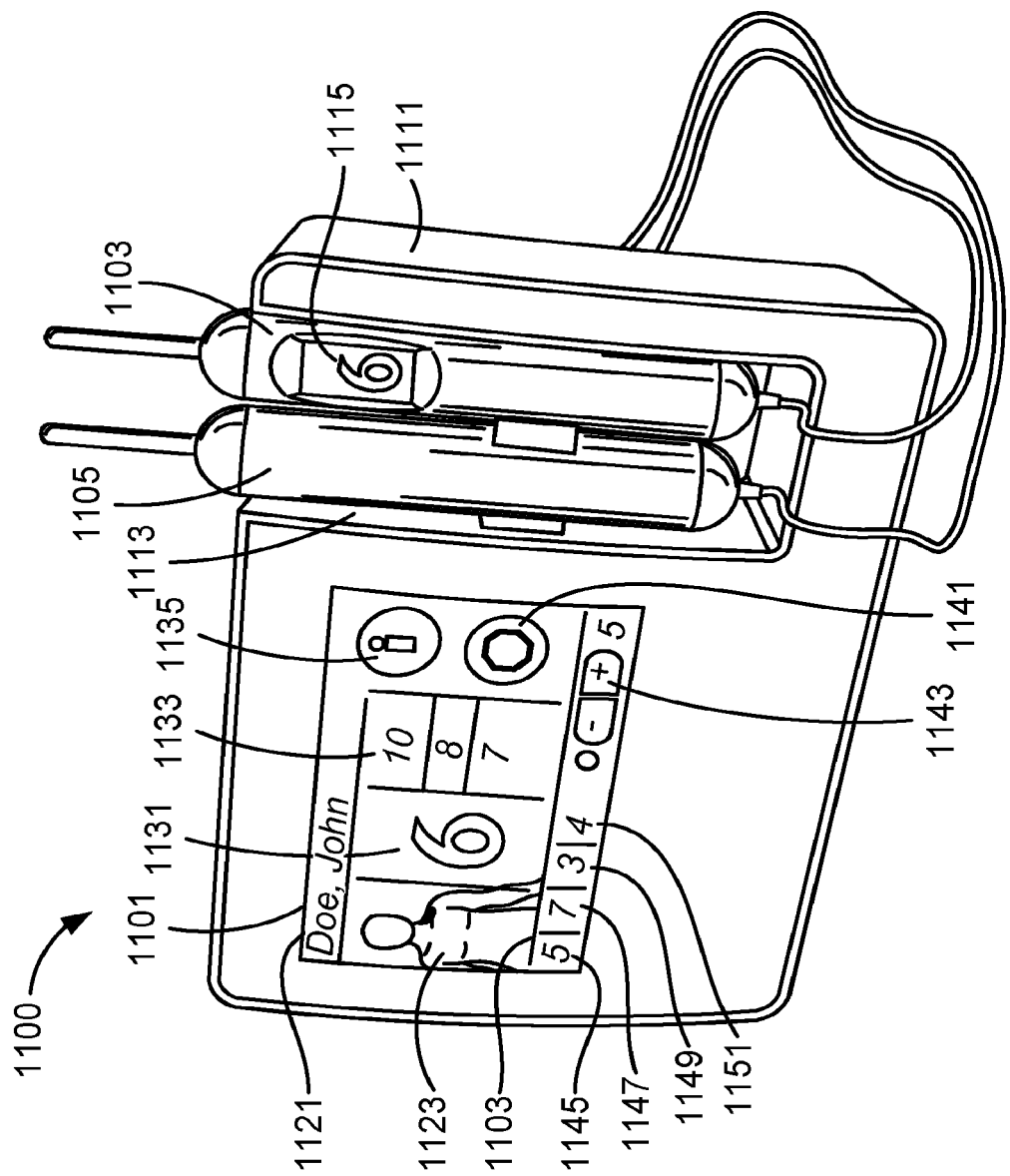
FIG. 11 is a perspective view of an alternate patient treatment unit with a touch screen.

FIG. 11 is a perspective view of an alternate patient treatment unit 1100 that includes a touch screen display 1101 that includes display of pre-treatment and real-time data to aid the clinician. The patient treatment unit 1100 also includes a primary probe 1103 and a secondary probe 1105 that operate similarly to the probes 103 and 105 in FIG. 1. The patient treatment unit includes a casing 1111 with a cradle 1113 to hold the primary and secondary probes 1103 and 1105. The primary probe 1105 includes an intensity display 1115 that displays the level of charge being currently applied.

The touch screen display 1101 incorporates many of the data displays explained above to assist the clinician during the treatment procedure. The display 1101 includes a patient name field 1121 and a instructional graphic 1123. The patient data associated with the patient name may be recalled from a database in the patient treatment unit 1100 in order to tailor the treatment to the particular patient. The instructional graphic 1123 may include a diagram of the locations on the body to place the probes 1103 and 1105. The status of the treatment unit 1100 may be determined from various data displayed on the display 1101. For example, the intensity of the pulses from the probes may be displayed in an intensity field 1131. Different values may be displayed in a test history field 1133. Other screens may be accessed by pressing an information button 1135.

The treatment unit 1100 may be controlled via various controls that may be activated by touching the display 1101. The procedure may be ended by pressing an end button 1141 on the display 1101. Other levels may be set using a plus/minus control 1143. The plus/minus control may be used in conjunction with a sensitivity field 1145, a tone field 1147, a cutoff field 1149 and a carrier field 1151 to set the respective levels of sensitivity (set at 5 in this example), tone (set at 7 in this example), cutoff (set at 3 in this example) and carrier (set at 4 in this example).

The system and methods disclosed may be used to treat conditions such as arthritis, post surgical pain, post surgical reduction of swelling, inflammation and bruising, Osgood Schlater Disease, treatment of organ transplant patients for the purpose of reducing organ rejection, adhesive capsilitus, MS, ALS, motor neuron disease, reduction of keloid scarring treatment of skin graft sites for better vascularization and better chance of successful graft improvement of circulation and oxygen saturation in compromised tissue and limbs, limb and digit reattachment for better chance of successful graft, improvement and normalization of conductivity in infarcted cardiac tissue, joint inflammation and injuries, fibromyalgia, reflex sympathetic dystrophy, neuralgia, peripheral neuropathy, macular degeneration, wounds and scleroderma. However, a library of tissue profiles and conductivity measurements may be employed in the system to develop a separate library of profiles for each patient as well as a baseline of healthy tissue types. While the present inventions have been described in connection with a number of exemplary embodiments and implementations, the present inventions are not so limited, but rather cover various modifications, and equivalent arrangements, which fall within the purview of prospective claims.

What is claimed is:

1. A patient treatment unit for analyzing and treating pain in human or animal tissues, the treatment unit comprising:
   a probe stimulus generator that outputs a sequence of electrical pulses, the electrical pulses having a pulse width and a pulse frequency, a peak pulse amplitude of approximately 190 V, and a maximum output current of about 8.9 mA, the probe stimulus generator controlling the pulse frequency and the pulse width of the electrical pulses;
   a primary spherical probe and a secondary spherical probe for contacting a body of a patient and electrically coupled to the probe stimulus generator to receive the sequence of electrical pulses;
   a body impedance analysis circuit that senses voltage or current via the primary spherical probe and the secondary spherical probe in real-time as the sequence of electrical pulses are applied to the tissues when the primary spherical probe and the secondary spherical probe are contacting the body of the patient;
   an interface module configured to wirelessly upload from a memory storage device a total elapsed treatment time stored in the memory device to an external system;
   a monitor device electrically coupled to the body impedance analysis circuit that provides an indication of the sensed voltage or current as an impedance measurement in real-time as the sequence of electrical pulses are applied to the tissues,
   wherein the pulse frequency of the electrical pulses is in a range of (i) 1 Hz-490 Hz±6% with 500 ohms to 1 mega-ohm of resistance across the primary spherical probe and the secondary spherical probe, or (ii) 10 kHz-20 kHz with 500 ohms to 1 mega-ohm of resistance across the primary spherical probe and the secondary spherical probe.

2. The patient treatment unit of claim 1, further comprising a storage device to store data representing the sensed impedance measurement.

3. The patient treatment unit of claim 1 further comprising a treatment counter circuit that detects and tracks an elapsed treatment time indicative of the time the primary spherical probe is receiving the sequence of electrical pulses.

4. The patient treatment unit of claim 1, wherein the monitor device electrically coupled to the body impedance analysis circuit includes an audio voice output that provides a voice indication of the sensed voltage or current.

5. The patient treatment unit of claim 1, wherein the display device displays a derivative of the impedance measurement graphically in real-time.

6. The patient treatment unit of claim 1 further comprising a memory device that stores initial conditions for the probe stimulus generator.

7. The patient treatment unit of claim 6, wherein the initial conditions for the probe stimulus generator include positions for placement of the primary spherical probe and the secondary spherical probe and wherein the display device displays the positions.

8. The patient treatment unit of claim 6, wherein the initial conditions for the probe stimulus generator include patient specific data and wherein the display device displays the patient specific data.

9. The patient treatment unit of claim 1 further comprising a memory device, the memory device storing data representing the real-time impedance measurement in correlation with data relating to the patient.

10. The patient treatment unit of claim 1 further comprising a security module, the security module allowing activation of the patient treatment unit on insertion of a datakey.

11. The patient treatment unit of claim 10, wherein the datakey has a predetermined validity time period for activation of the patient treatment unit.

12. The patient treatment unit of claim 10, wherein the treatment unit stores patient data on the inserted datakey.

13. The patient treatment unit of claim 1, wherein the monitor device measures feedback from the primary spherical probe and the secondary spherical probe to determine penetration depth.

14. The patient treatment unit of claim 1, wherein the display device is a touch screen having touch screen controls to control the probe stimulus generator.

15. A method of displaying real-time impedance data comprising:

outputting a sequence of electrical pulses via a probe stimulus generator, the electrical pulses having a pulse width, a pulse frequency, a peak pulse amplitude of approximately 190 V, and a maximum output current of about 8.9 mA;

receiving the electrical pulses in a primary spherical probe and a secondary spherical probe; contacting a body of a patient with the primary spherical probe and the secondary spherical probe;

sensing voltage or current via the primary spherical probe and the secondary spherical probe in real-time as the sequence of electrical pulses are applied to the tissues when the primary spherical probe and the secondary spherical probe are contacting the body of the patient via a body impedance analysis circuit;

providing an indication of the sensed voltage or current as an impedance measurement in real-time as the sequence of electrical pulses are applied to the tissues; and wirelessly uploading from a memory storage device a total elapsed treatment time to an external system;

wherein the pulse frequency of the electrical pulses is in a range of (i) 1 Hz-490 Hz±6% with 500 ohms to 1 mega-ohm of resistance across the primary spherical probe and the secondary spherical probe, or (ii) 10 kHz-20 kHz with 500 ohms to 1 mega-ohm of resistance across the primary spherical probe and the secondary spherical probe.

16. A patient treatment unit for analyzing and treating pain in human or animal tissues, the treatment unit comprising:

a probe stimulus generator including a high voltage generator, a low voltage control circuit that controls the shape of pulses generated by the high voltage generator, the low voltage control circuit being isolated from the high voltage generator, the probe stimulus generator outputting a sequence of electrical pulses, the electrical pulses having a pulse width and a pulse frequency, a peak pulse amplitude of approximately 190 V, and a maximum output current of about 8.9 mA, the probe stimulus generator controlling the pulse frequency and the pulse width of the electrical pulses; and a primary vibrating spherical probe and a secondary spherical probe for contacting a body of a patient and electrically coupled to the probe stimulus generator to receive the sequence of electrical pulses, wherein the pulse frequency of the electrical pulses is in a range of (i) 1 Hz-490 Hz±6% with 500 ohms to 1 mega-ohm of resistance across the primary vibrating spherical probe and the secondary spherical probe, or (ii) 10 kHz-20 kHz with 500 ohms to 1 mega-ohm of resistance across the primary vibrating spherical probe and the secondary spherical probe.

17. The patient treatment unit of claim 1, wherein the primary spherical probe is a primary vibrating spherical probe.

18. The method of claim 15, wherein the primary spherical probe is a primary vibrating spherical probe.

19. The method of claim 15, further comprising causing to be displayed graphically on a video display of the patient treatment unit or on an external video display guided, malady-specific, treatment starting points.

* * * * *